(12) United States Patent
Uji et al.

(10) Patent No.: US 10,349,826 B2
(45) Date of Patent: Jul. 16, 2019

(54) IMAGE PROCESSING APPARATUS, IMAGE PROCESSING METHOD, AND STORAGE MEDIUM

(71) Applicant: CANON KABUSHIKI KAISHA, Tokyo (JP)

(72) Inventors: Akihito Uji, Kyoto (JP); Hiroyuki Sekiguchi, Kyoto (JP); Yoshihiko Iwase, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/796,384

(22) Filed: Oct. 27, 2017

(65) Prior Publication Data

US 2018/0049635 A1 Feb. 22, 2018

Related U.S. Application Data

(63) Continuation of application No. 15/150,826, filed on May 10, 2016, now Pat. No. 9,826,896.

(30) Foreign Application Priority Data

May 14, 2015 (JP) ................................. 2015-099470

(51) Int. Cl.
*A61B 3/14* (2006.01)
*A61B 3/00* (2006.01)
*A61B 3/10* (2006.01)
*A61B 3/12* (2006.01)

(52) U.S. Cl.
CPC .......... *A61B 3/0025* (2013.01); *A61B 3/0033* (2013.01); *A61B 3/0058* (2013.01); *A61B 3/102* (2013.01); *A61B 3/1225* (2013.01)

(58) Field of Classification Search
CPC ........... A61B 3/14; A61B 3/0025; A61B 3/12; A61B 3/102; A61B 3/0058
USPC ......................................................... 351/206
See application file for complete search history.

(56) References Cited

U.S. PATENT DOCUMENTS

| 9,232,887 B2 * | 1/2016 | Goto | G01B 9/0203 |
| 9,700,199 B2 * | 7/2017 | Tomatsu | A61B 3/0025 |
| 9,826,896 B2 * | 11/2017 | Uji | A61B 3/0025 |
| 9,848,769 B2 * | 12/2017 | Miyasa | G06T 7/0012 |

(Continued)

FOREIGN PATENT DOCUMENTS

| CN | 103211574 A | 7/2013 |
| CN | 103222848 A | 7/2013 |
| CN | 103767679 A | 5/2014 |

(Continued)

OTHER PUBLICATIONS

Takahashi, "Optical Coherence Tomography Findings of Macular Hole", Journal of the Eye, May 2009, vol. 26, No. 5; with translation of Office Action showing relevance of cited document (Takahashi).

*Primary Examiner* — Mohammed A Hasan
(74) *Attorney, Agent, or Firm* — Canon USA Inc., IP Division

(57) ABSTRACT

An image processing apparatus includes a detecting unit configured to execute structural analysis on a tomographic image acquired by an acquiring unit and detect an abnormal portion of the eye; and a display control unit configured to cause a displaying unit to display a finding of the abnormal portion detected by the detecting unit, as a sentence or a word in a manner superimposed on the tomographic image.

22 Claims, 21 Drawing Sheets

(56) References Cited

U.S. PATENT DOCUMENTS

2012/0288175 A1* 11/2012 Iwase ..................... G06T 7/33
                                                              382/131

FOREIGN PATENT DOCUMENTS

| JP | H07-031591 A | 2/1995 |
| JP | 2002-306415 A | 10/2002 |
| JP | 2011-092702 A | 5/2011 |
| JP | 2012-110618 A | 6/2012 |
| JP | 2012-235835 A | 12/2012 |
| WO | 2010/134278 A1 | 11/2010 |

* cited by examiner

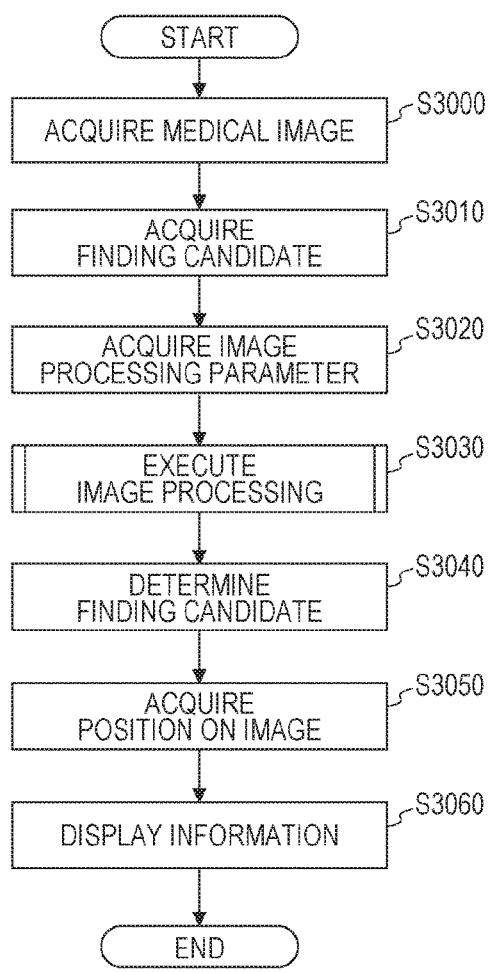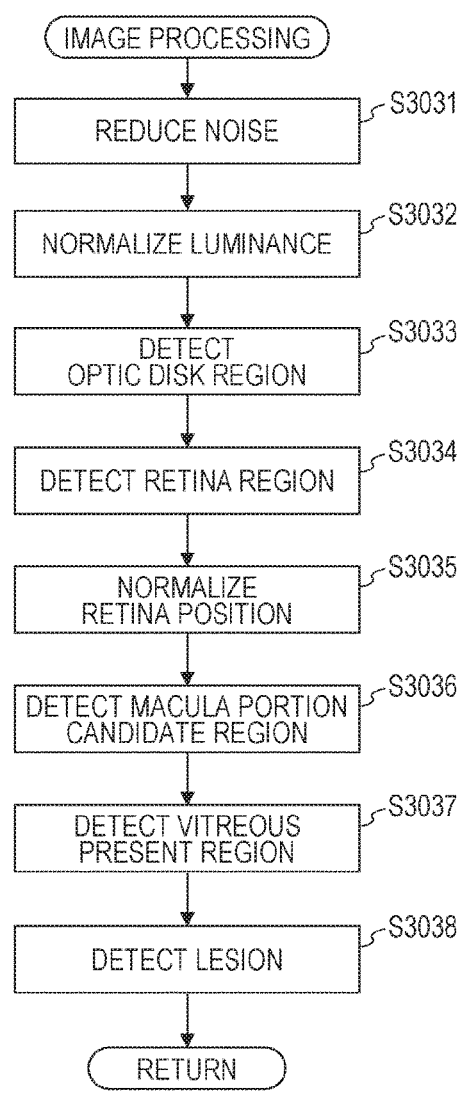

FIG. 5A

| PORTION | IMAGE TYPE | FINDINGS |
|---|---|---|
| RETINA MACULA PORTION | OCT IMAGE | FOVEAL CYSTOID HOLE |
| | | FIBER LAYER CYSTOID HOLE |
| | | ... |
| | | MACULAR HOLE |
| RETINA OPTIC DISK PORTION | OCT IMAGE | LARGE OPTIC DISK CUP |
| ... | ... | ... |

FIG. 5B

| FINDINGS | IMAGE TYPE | IMAGE PROCESSING PARAMETER |
|---|---|---|
| FOVEAL CYSTOID HOLE | OCT IMAGE | EXTRACT X: 40% TO 60%, Z: 30% TO 70%, PIXEL VALUE: 10 OR SMALLER |
| FIBER LAYER CYSTOID HOLE | OCT IMAGE | EXTRACT X: 25% TO 75%, Z: 30% TO 70%, PIXEL VALUE: 10 OR SMALLER |
| POSTERIOR VITREOUS DETACHMENT | OCT IMAGE | EXECUTE THINNING ON RANGE WITH Z: LARGER THAN ILM |
| ... | | |
| MACULAR HOLE | OCT IMAGE | EXECUTE REGION EXPANSION ON X: 40% TO 60%, Z: PIXEL ADJACENT TO RPE, PIXEL VALUE: 10 OR SMALLER |
| | FUNDUS IMAGE | PIXEL VALUE: G COMPONENT BEING 35 OR SMALLER, RING FILTER (R =5) |
| ... | | |

FIG. 14

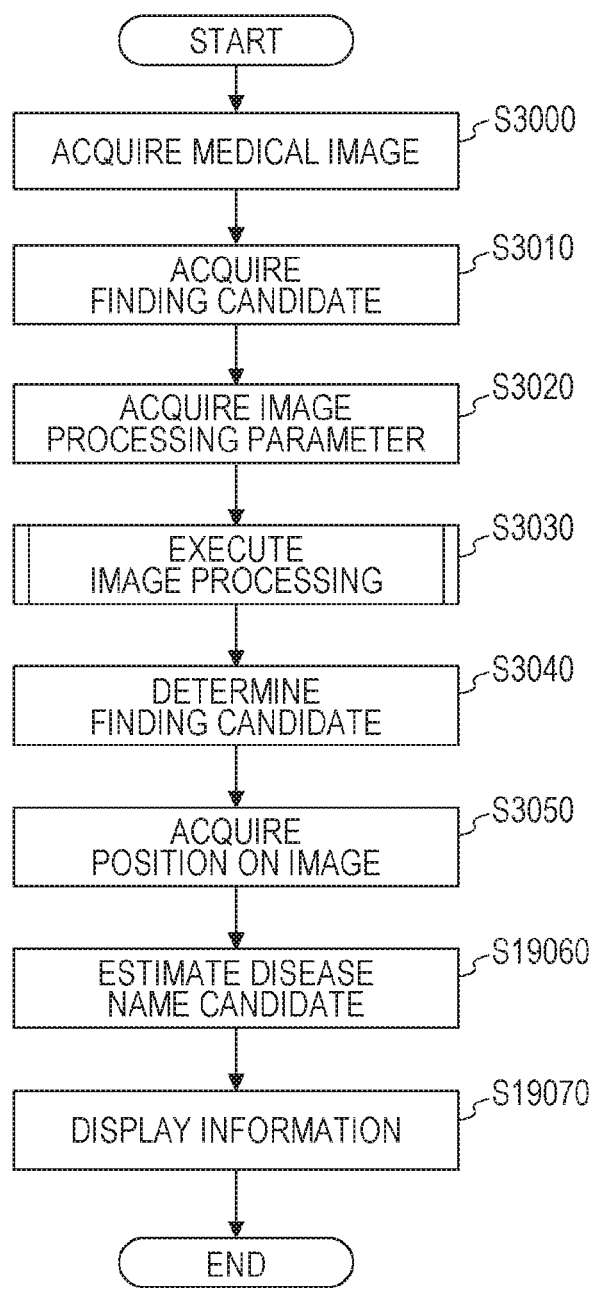

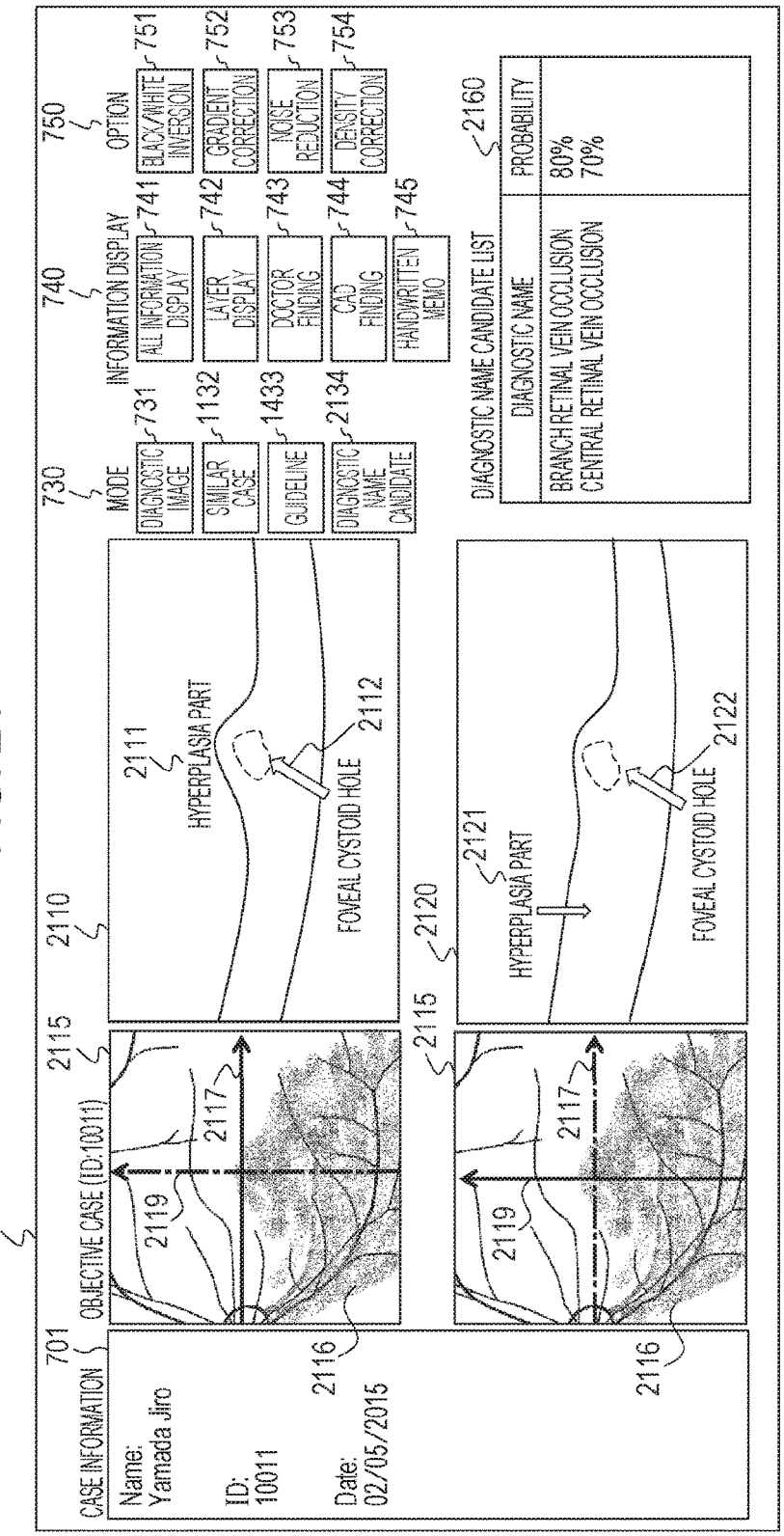

IMAGE PROCESSING APPARATUS, IMAGE PROCESSING METHOD, AND STORAGE MEDIUM

CROSS-REFERENCE TO RELATED APPLICATIONS

This application is a Continuation of co-pending U.S. patent application Ser. No. 15/150,826, filed May 10, 2016, which claims foreign priority benefit of Japanese Patent Application No. 2015-099470 filed May 14, 2015. The above-named patent applications are hereby incorporated by reference herein in their entirety.

BACKGROUND OF THE INVENTION

Field of the Invention

The disclosed technology relates to an image processing apparatus, an image processing method, and a storage medium.

Description of Related Art

Japanese Patent Application Laid-Open No. 2010-268916 discloses an anterior ocular segment observation device for automatically extracting a finding (abnormality in form) from a tomographic image of an anterior eye portion, and displaying the content of the abnormality.

However, Japanese Patent Application Laid-Open No. 2010-268916 does not disclose how to associate the content of the abnormality with the tomographic image and display both. It may be difficult for a doctor to easily recognize the relationship between the content of the abnormality and the tomographic image.

SUMMARY OF THE INVENTION

The disclosed technology is made to address the above-described drawbacks of conventional technology, and provides display that allows the relationship between the finding and the tomographic image to be easily recognized.

The present disclosure provides an image processing apparatus including an acquiring unit configured to acquire a tomographic image of an eye to be inspected; a detecting unit configured to execute structural analysis on the tomographic image acquired by the acquiring unit and detect an abnormal portion of the eye; and a display control unit configured to cause a displaying unit to display a finding of the abnormal portion detected by the detecting unit, as a sentence or a word in a manner superimposed on the tomographic image.

The disclosed technology may also attain an advantageous effect which is derived by respective configurations of embodiments for implementing the invention (described later) but which is not provided by related art.

Further features of the present invention will become apparent from the following description of exemplary embodiments with reference to the attached drawings.

BRIEF DESCRIPTION OF THE DRAWINGS

FIGS. 3A and 3B provide flowcharts showing examples of processing of the medical diagnosis support apparatus.

FIGS. 5A and 5B provide illustrations showing examples of table information.

FIG. 14 is an illustration showing an example display of a displaying unit according to a third embodiment.

FIG. 19 is a flowchart showing an example of processing of the medical diagnosis support apparatus.

FIG. 21 is an illustration showing an example display of a displaying unit according to the fifth embodiment.

DESCRIPTION OF THE EMBODIMENTS

An image processing apparatuses according to embodiments are described below with reference to the accompanying drawings. It is to be noted that configurations described in the following embodiments are merely examples, and the present invention is not limited to the configurations disclosed in the specification and drawings.

First Embodiment

A diagnosis support apparatus (an image processing apparatus) according to a first embodiment acquires a medical image of a subject or part thereof being an object of a diagnosis, provides support information on the medical image by using the image processing result of the acquired medical image, and hence supports a diagnosis of the subject based on information relating to the medical image.

In this embodiment, a case example is described, in which image processing is executed on an optical coherence tomographic image (hereinafter, merely referred to as tomographic image) in the ophthalmology field. In this example, the image processing apparatus identifies a finding on the basis of the image processing result, and the information of such finding is provided on the tomographic image. In this embodiment, it is assumed that the tomographic image is a single two-dimensional fundus image captured in a direction passing through an optic disk and a fovea (a macula portion). Hereinafter, an image captured in the direction passing through the optic disk and the fovea may be occasionally referred to as an H-scan image. Of course, the object of the image processing is not limited to the aforementioned object. For example, the tomographic image may be an image including at least one of the optic disk and the macula portion, or may be an image not including the optic disk or the macula portion. Also, any of findings etc. described below is merely an example for describing the procedure of the diagnosis support apparatus. In the embodiment described below, image processing mainly on a fundus tomographic image as a medical image is described; however, image processing described below may be applied to a tomographic image of an anterior eye portion.

Figure 1:
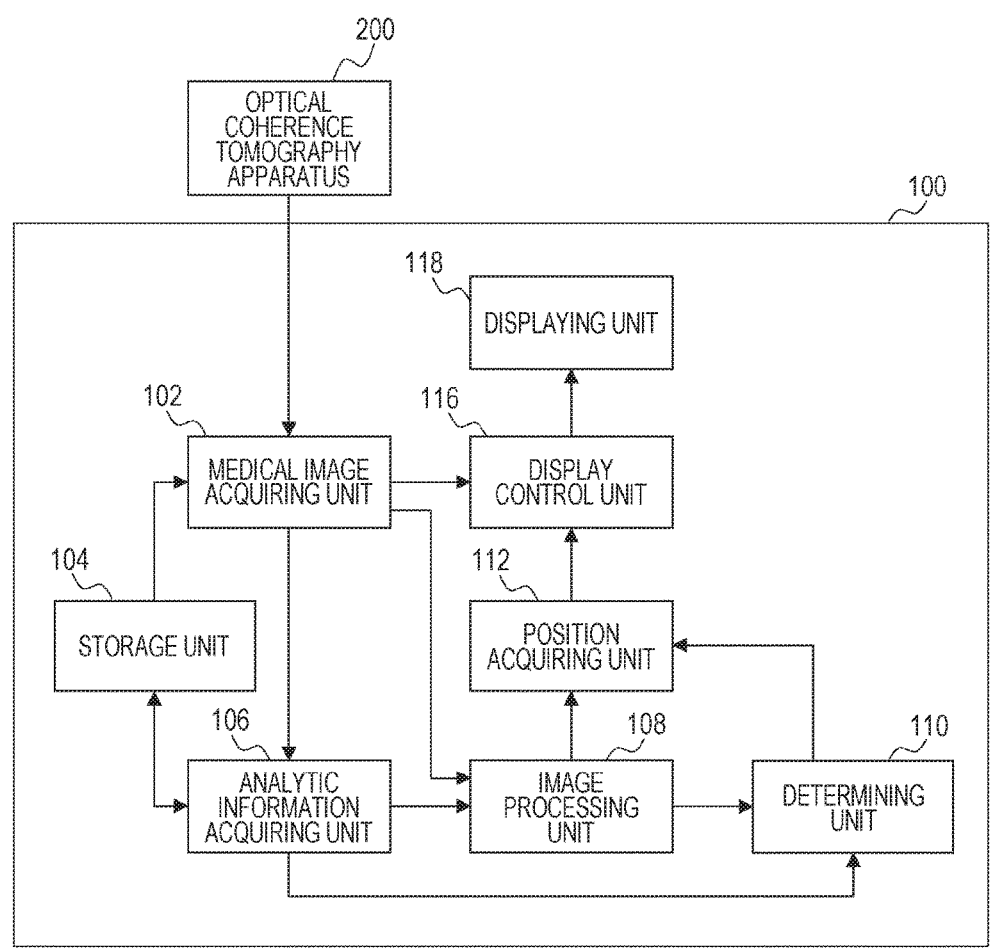
FIG. 1 is an illustration showing an example of a functional configuration of a medical diagnosis support apparatus.

FIG. 1 is an illustration showing an example of a functional configuration of a diagnosis support apparatus 100 according to the first embodiment. The diagnosis support apparatus 100 is, for example, a desktop personal computer (PC), a notebook PC, or a tablet PC. The diagnosis support apparatus (the image processing apparatus) 100 according to this embodiment is connected with an optical coherence tomography (OCT) apparatus 200 in a wired or wireless manner. The optical coherence tomography apparatus 200 is formed of, for example, a spectral-domain-OCT (SD-OCT), swept-source-OCT (SS-OCT), or a polarization-sensitive-OCT (PS-OCT). Since the optical coherence tomography apparatus 200 is a known apparatus, the detailed description thereof is omitted. The optical coherence tomography apparatus 200 acquires a tomographic image (that is, a medical image) indicative of a cross section of a retina by using interference between return light obtained by irradiating a fundus with near-infrared light, and reference light. Then, the optical coherence tomography apparatus 200 outputs the acquired medical image, and data relating to imaging information (image type, imaging portion, imaging size, scan pattern, etc.) to the diagnosis support apparatus 100 through communication with a universal serial bus (USB), a local area network (LAN), etc. The imaging information includes, for example, an image type of "OCT," an imaging portion of "macula portion," an imaging size of "12 mm," and a scan pattern of "line scan," etc. Considering another example, the imaging information includes an image type of "OCT," an imaging portion of "optic disk portion," an imaging size of "6 mm," and a scan pattern of "3D scan," etc. The imaging information is not limited thereto, and not all information described above is necessary. The image type does not have to be only OCT, and the type of OCT, for example, SD-OCT, SS-OCT, or PS-OCT may be included in the information. Also, the unit of the imaging size does not have to be a length, and may be an angle or area. The image type is, for example, a type of a medical image in accordance with modality, such as an OCT image (a tomographic image obtained by the optical coherence tomography), a plain radiographic image, or a computed tomographic (CT) image.

The diagnosis support apparatus 100 includes a medical image acquiring unit 102, a storage unit 104, an analytic information acquiring unit 106, an image processing unit 108, a determining unit 110, a position acquiring unit 112, a display control unit 116, and a displaying unit 118. A CPU 1001 illustrated in FIGS. 2A and 2B functions as the medical image acquiring unit 102, the analytic information acquiring unit 106, the processing unit 108, the determining unit 110, the position acquiring unit 112, and the display control unit 116.

The medical image acquiring unit 102 acquires a medical image and data relating to imaging information on the medical image transmitted from the optical coherence tomography apparatus 200 to the diagnosis support apparatus 100. The medical image and the imaging information on the medical image may be stored in the storage unit 104, and may be read from the storage unit 104 in response to a request from a user. Alternatively, an external storage device (not shown), such as a solid state disk (SSD), a hard disk drive (HDD), a floppy disk drive (FDD), a USB memory, a compact disc (CD) drive, a digital versatile disc (DVD) drive, a magneto-optical (MO) disk drive, or a Zip drive may be connected with the diagnosis support apparatus 100, and the medical image acquiring unit 102 may acquire the information from the external storage device. In this embodiment, as an example, it is assumed that the medical image acquiring unit 102 acquires the tomographic image and the imaging information on the tomographic image from the optical coherence tomography apparatus 200. That is, the medical image acquiring unit 102 corresponds to an example of an acquiring unit configured to acquire a tomographic image of an eye to be inspected.

The medical image acquiring unit 102 outputs the acquired medical image to the image processing unit 108 and the display control unit 116, and outputs the imaging information on the captured medical image to the analytic information acquiring unit 106.

The storage unit 104 stores first table information including a plurality of finding candidates to be respectively applied to portions of the medical image being a diagnosis object, and second table information including image processing parameters respectively corresponding to the finding candidates. The image processing parameters each are a parameter used in image processing for specifying each of the plurality of finding candidates. The details of the first table information and the second table information are described later with reference to FIGS. 5A and 5B.

The analytic information acquiring unit 106 acquires analytic information (image processing parameters) from the storage unit 104, on the basis of information on the type and portion of the medical image acquired by the medical image acquiring unit 102. To be specific, the analytic information acquiring unit 106 acquires the plurality of finding candidates corresponding to the type and portion of the medical image acquired from the medical image acquiring unit 102, from the first table information stored in the storage unit 104. Further, the analytic information acquiring unit 106 acquires the image processing parameters respectively corresponding to the candidates from the second table information stored in the storage unit 104 on the basis of the plurality of acquired finding candidates. The analytic information acquiring unit 106 outputs the plurality of finding candidates to the determining unit 110, and outputs the image processing parameters to the image processing unit 108.

The image processing unit 108 executes image processing on the medical image on the basis of the medical image acquired by the medical image acquiring unit 102 and the image processing parameters acquired by the analytic information acquiring unit 106. The image processing unit 108 outputs the result of the image processing to the determining unit 110 and the position acquiring unit 112.

The determining unit 110 determines which one of the plurality of finding candidates is present in the medical image on the basis of the plurality of finding candidates acquired by the analytic information acquiring unit 106 and the result of the image processing executed by the image processing unit 108. That is, the determining unit 110 determines which finding candidate corresponds to the medical image. The determining unit 110 outputs the determination result to the position acquiring unit 112.

The position acquiring unit 112 acquires information indicative of a position of a lesion or disease (an abnormal portion) in the medical image corresponding to the finding on the basis of the result of the image processing executed by the image processing unit 108 and the finding candidate determined as the corresponding finding by the determining unit 110. The acquisition of the information indicative of the position is described later. The position acquiring unit 112 associates the acquired information indicative of the position with the finding candidate determined as the corresponding finding by the determining unit 110, and outputs the information to the display control unit 116.

The display control unit 116 controls display on the basis of the medical image acquired by the medical image acquiring unit 102 and the information indicative of the position in the medical image acquired by the position acquiring unit 112 and associated with the finding candidate determined as the corresponding finding. The position in the medical image associated with the finding candidate is the position in the medical image of the lesion (the abnormal portion) corresponding to the finding. To be specific, the display control unit 116 causes the displaying unit 118 to display the medical image and to superimpose the finding candidate determined as the corresponding finding on the displayed medical image. The display control unit 116 may cause the displaying unit 118 to display an indication (a marker or the like, described later) indicative of the position of the finding.

The displaying unit 118 displays the display content controlled by the display control unit 116. The displaying unit 118 is included in the diagnosis support apparatus 100; however, it is not limited thereto. The displaying unit 118 may be provided separately from the diagnosis support apparatus 100.

At least part of the respective units of the diagnosis support apparatus 100 illustrated in FIG. 1 may be realized as an independent device. Alternatively, the respective units may be realized as software configured to realize respective functions. In this embodiment, it is assumed that the respective units each are realized by software.

Figure 2A:
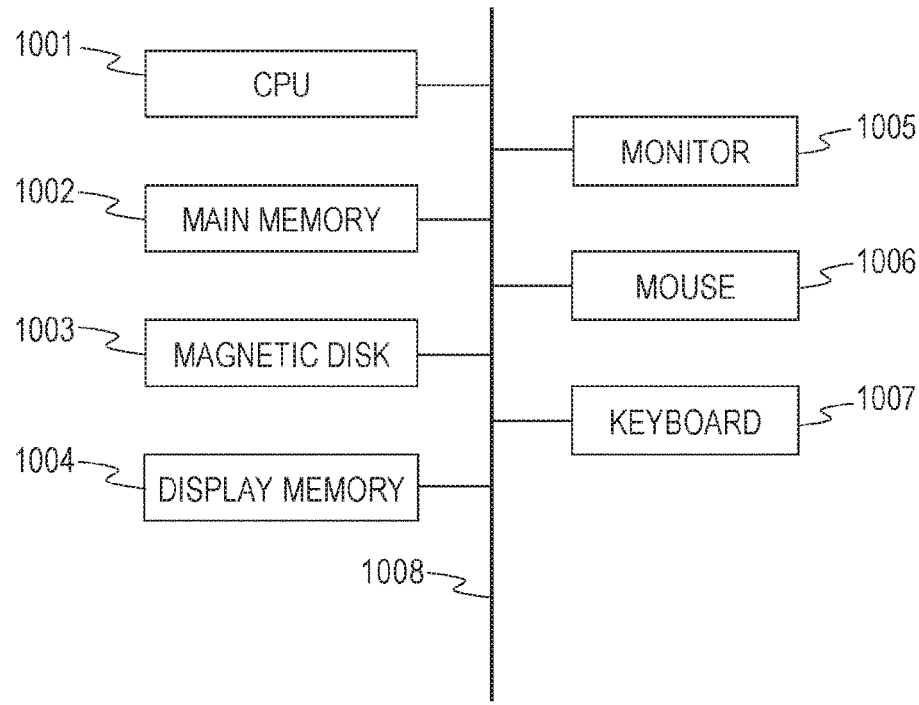
FIGS. 2A and 2B provide illustrations showing examples of hardware configurations of the medical diagnosis support apparatus.
Figure 2B:
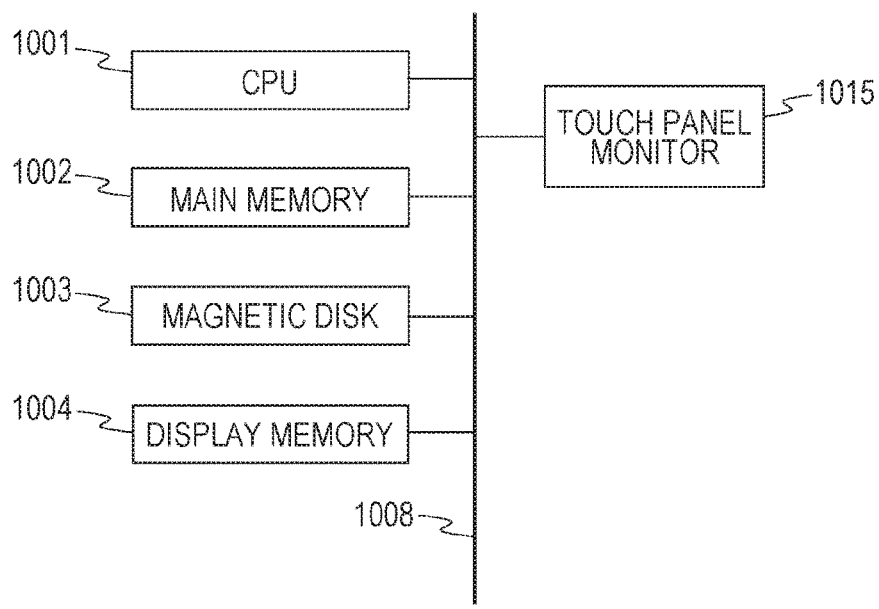

FIGS. 2A and 2B provide illustrations showing examples of hardware configurations of the diagnosis support apparatus 100. A central processing unit (CPU) 1001 mainly controls operations of respective components. A main memory 1002 stores a control program executed by the CPU 1001, and provides a work area during execution of the program by the CPU 1001. A magnetic disk 1003 stores an operating system (OS), device drivers of peripheral devices, and programs for realizing various application software including a program for executing processing etc. (described later). The CPU 1001 executes the programs stored in the main memory 1002 and/or the magnetic disk 1003, and hence realizes the functions (the software) of the diagnosis support apparatus 100 illustrated in FIG. 1 and processing in a flowchart (described later).

A display memory 1004 temporarily stores display data. A monitor 1005 is an example of the displaying unit 118, and is, for example, a cathode-ray tube (CRT) monitor or a liquid crystal monitor. The monitor 1005 displays an image, text, etc. on the basis of data from the display memory 1004. A mouse 1006 and a keyboard 1007 respectively receive an input with pointing and an input with characters by a user. The above-described components are connected with each other by a common bus 1008 to enable communication among the components.

Alternatively, the monitor 1005, the mouse 1006, and the keyboard 1007 in FIG. 2A may be replaced with a touch panel monitor 1015 as shown in FIG. 2B. The touch panel monitor 1015 is, for example, a touch panel liquid crystal display (LCD) monitor. The touch panel monitor 1005 displays an image and text on the basis of data from the display memory 1004, and receives an input with pointing and an input with characters by the user. The mouse 1006 and the keyboard 1007 may be provided in addition to the touch panel monitor 1015. If a patient is selected with the apparatus including the touch panel monitor 1015, desirable patient information is temporarily selected by an operator tapping one patient information among a plurality of pieces of patient information (patient identifications (IDs)) displayed on the displaying unit 118. Then, after the temporal selection, the patient information is selected by the operator swiping the patient information. The position on the touch panel to be swiped may be a position different from the position at which the desirable patient information is displayed. The CPU 1001 detects the operations of tapping and swiping and selects the desirable patient information. That is, the CPU 1001 is an example of a selecting unit configured to temporarily select the one patient information if the one patient information among a plurality of pieces of patient information displayed in a list form by a displaying unit is tapped, and select the one patient information if swiping is made after the tapping. When the patient information is selected, the medical image acquiring unit 102 acquires a tomographic image corresponding to the patient information selected by the selecting unit. By employing such a selection method for patient information, patient information corresponding to the intention of the operator can be easily selected from a plurality of pieces of patient information indicated with small characters. For example, if patient information is selected by double tapping, it may be difficult to double-tap the same position, and hence difficult to quickly select desirable patient information. The above-described selection method of tapping and swiping patient information addresses the difficulty of double-tapping the same position.

An example of processing executed by the diagnosis support apparatus 100 is described next with reference to a flowchart in FIG. 3A. FIG. 3A is a flowchart showing an example of processing executed by the diagnosis support apparatus 100. In this embodiment, the processing shown in FIG. 3A is realized by the CPU 1001 executing the programs stored in the main memory 1002, for realizing the functions of the respective units of the diagnosis support apparatus 100.

In step S3000, the medical image acquiring unit 102 acquires a medical image transmitted from the optical coherence tomography apparatus 200, information relating to the type of the captured medical image, and information relating to the portion of the medical image. In the example of this embodiment, the medical image is a tomographic image (an H-scan image) captured by the optical coherence tomography apparatus 200, and hence the medical image acquiring unit 102 acquires "OCT" as the information relating to the type of the medical image, and "macula portion" as the information relating to the portion of the medical image. It is to be noted that the information relating to the portion of the medical image is not limited to "macula portion."

In step S3010, the analytic information acquiring unit 106 acquires a plurality of corresponding finding candidates from the first table information stored in the storage unit 104, on the basis of the information relating to the type of the medical image and the information relating to the portion of the medical image acquired in step S3000.

FIG. 5A is an illustration showing an example of the first table information stored in the storage unit 104. This table information stores a fundus portion of an eye to be inspected and information on image type in an associated manner, and the information on image type and a plurality of finding candidates in an associated manner. In the example of this embodiment, since the portion is "macula portion" and the image type is "OCT," the analytic information acquiring unit 106 acquires a plurality of finding candidates, such as a foveal cystoid hole, a fiber layer cystoid hole, and a macular hole. This is because a finding to be determined is different depending on the portion and image type. It is to be noted that finding candidates associated with an image type are not necessarily plural finding candidates. For example, if the portion is classified into smaller sections, the number of finding candidates to be associated with the image type may be one. Alternatively, in the example in FIG. 5A, the image type may be omitted, and a portion may be associated with a finding. That is, the first table information is not limited to the example shown in FIG. 5A.

In step S3020, the analytic information acquiring unit 106 acquires image processing parameters required for respectively specifying the plurality of finding candidates from the second table information of the storage unit 104 on the basis of the plurality of finding candidates acquired in step S3010. In this embodiment, it is assumed that the analytic information acquiring unit 106 uses information relating to the type of the medical image acquired in step S3000 in addition to the information on the finding candidate, to acquire the image processing parameter.

FIG. 5B is an illustration showing an example of the second table information stored in the storage unit 104. For example, if the finding is "fiber layer cystoid hole" and the image type is "OCT," an image processing parameter of "X: 25% to 75%, Z: 30% to 70%, pixel value: 10 or smaller" is associated with the finding. The analytic information acquiring unit 106 acquires such image processing parameters respectively for the plurality of finding candidates acquired in step S3010. In this case, Z: 30% to 70% represents, for example, a retina region in a tomographic image.

In the example of this embodiment, since the type of the medical image is "OCT," "foveal cystoid hole" is acquired as the finding candidate in step S3010. Therefore, the analytic information acquiring unit 106 acquires the image processing parameter of "X: 40% to 60%, Z: 30% to 70%, pixel value: 10 or smaller" from the second table information.

Alternatively, in the example in FIG. 5B, the image type may be omitted, and a finding may be associated with an image processing parameter. That is, the second table information is not limited to the example shown in FIG. 5B.

In step S3030, the image processing unit 108 executes image processing on the medical image on the basis of the medical image acquired in step S3000 and the image processing parameter acquired in step S3020. In the example described below, it is assumed that a low reflection region corresponding to the background of a monochrome image with 256 gradations is black (pixel value being 0).

Figure 4A:
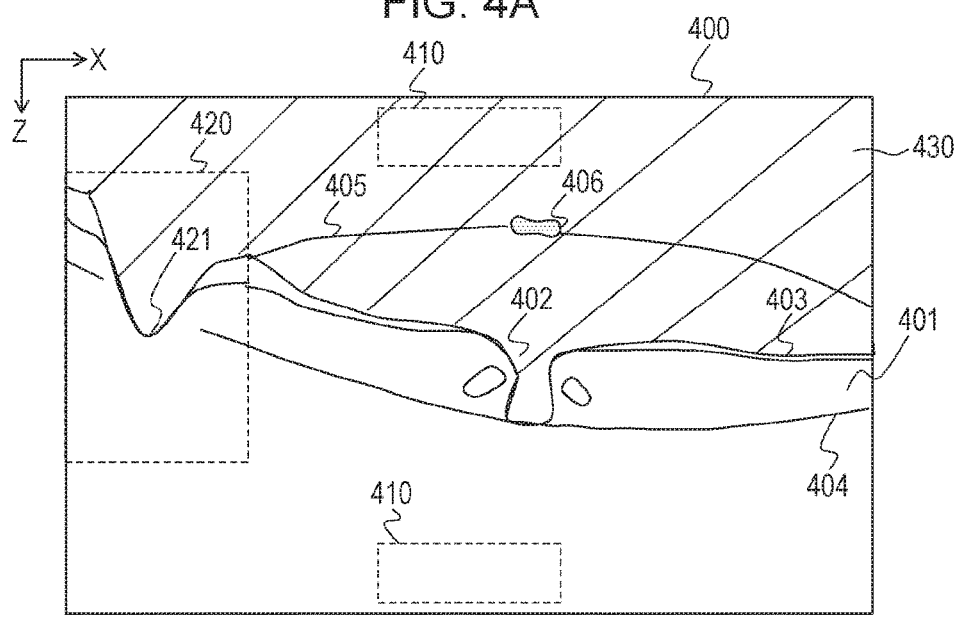
FIGS. 4A to 4C provide illustrations showing examples of image processing.

The image processing is described with reference to a flowchart in FIG. 3B and FIGS. 4A to 4C. FIG. 3B is a flowchart showing specification of an example of the processing in step S3030. FIG. 4A is an illustration showing an example of a tomographic image. In FIG. 4A, reference sign 400 denotes a tomographic image, 401 denotes a retina layer region, 402 denotes a macula portion, 403 denotes an upper portion of an internal limiting membrane (ILM) or a nerve fiber layer (NFL), and 404 denotes retinal pigment epithelium (RPE). Further, in FIG. 4A, reference sign 405 denotes posterior vitreous detachment, 406 denotes a lid, 410 denotes a background region, 420 denotes an optic disk region, 421 denotes an optic disk portion, and 430 of an oblique line region above the retina layer denotes a vitreous body. As shown in FIG. 4A, the tomographic image includes a region indicative of the retina and the background region 410 (a region other than the retina).

Figure 4B:
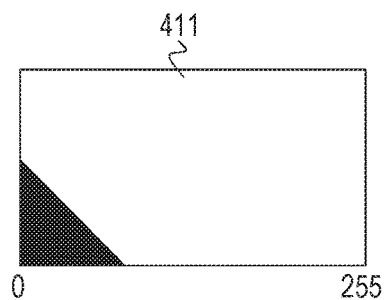
Figure 4C:
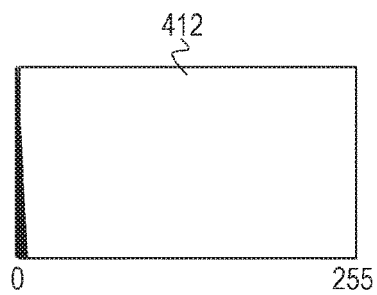

In step S3031, the image processing unit 108 reduces noise from the tomographic image. In OCT imaging, during line scan or cross scan, the optical coherence tomography apparatus 200 executes tracking on an eye, and captures an image a plurality of times at the spatially same position. Then, a plurality of tomographic images captured at the same position are positioned (aligned), and averaging processing is executed on a plurality of corresponding pixels among the tomographic images. Accordingly, processing of noise reduction is executed on the tomographic images. In this case, it is assumed that the image processing unit 108 has already executed the positioning and the averaging processing on the tomographic images. As described above, since the image processing unit 108 executes the positioning and the averaging processing on the tomographic images captured the plurality of times, random noise is reduced. However, the similarity among the tomographic images during the positioning is decreased depending on the state of the eye to be inspected (defective fixation) during capturing. Hence, the averaging processing may not be executed on a predetermined number of tomographic images with similarities lower than a predetermined threshold. In this case, the noise level of images may be different depending on the number of tomographic images used for averaging. For example, FIGS. 4B and 4C show histograms of the region 410 in FIG. 4A. FIG. 4B is an example of a histogram 411 with a small number of images for the averaging processing (for example, one to three images). FIG. 4C is an example of a histogram 412 with a large number of images for the averaging processing (for example, ten images or more). Black portions in FIGS. 4B and 4C indicate histograms of the region 410. In each of FIGS. 4B and 4C, the vertical axis indicates the frequency and the horizontal axis indicates the luminance. As shown in the drawings, the noise is different depending on the number of tomographic images used for the averaging processing. Owing to this, the image processing unit 108 changes the parameter for noise reduction depending on the noise level. As a method of reducing noise from a tomographic image, for example, the image processing unit 108 first estimates noise from the region 410 (at least one of the vitreous body and sclera) corresponding to the background of the retina inner layer of a tomographic image. Then, the image processing unit 108 changes the filter size of a median filter, a Gaussian filter, or the like, used for noise reduction depending on the noise quantity. The image processing unit 108 increases the filter size if the noise quantity is large, and decreases the filter size if the noise quantity is small. Accordingly, image blurring by the noise reduction is decreased. If the noise quantity is large, the noise can be reduced. Also, the upper limit value of the filter size is desirably determined by the physical size per pixel. For example, a case of capturing in a 1-mm range with 100 lines of A scan and a case of capturing in a 1-mm range with 50 lines of A scan may have different image ranges corresponding to image pixels. That is, when the parameter of the noise reducing filter in the X-direction is set at 10, the physical size per pixel is about 0.1 mm in the case of capturing with 100 lines; however, the physical size per pixel is about 0.2 mm in the case of capturing with 50 lines. Hence, the parameter is adjusted to execute the noise reduction in the equivalent range.

In step S3032, the image processing unit 108 normalizes the density of the tomographic image. This is processing of matching the density level of luminance as far as possible between a tomographic image being a reference and a tomographic image being a processing object. Accordingly, the difference in brightness of an image is absorbed for each eye to be inspected. A method of correcting density may be a method of matching histograms between the reference image and the object image, or a method of matching density levels by using a density conversion table. Also, in a case of a tomographic image with the background being white (the pixel value being 255), the image processing unit 108 executes black/white inversion. In this image processing, description is given for the case with the background of the tomographic image being black. However, it is not limited thereto. The case with the background of the tomographic image being white may be considered as the reference. In this case, the pixel value set at 10 or smaller as the threshold for the image processing parameter may be a pixel value being 245 or larger.

In step S3033, the image processing unit 108 detects the optic disk portion. In a case relating to a macular disease, the optic disk region is eliminated and processing is executed. In a case relating to the optic disk portion, the optic disk portion is extracted. For example, diagnosis support for a macular disease is described here. In this case, the image processing unit 108 eliminates the optic disk region from the tomographic image. As shown in FIG. 4A, the optic disk portion has a large cup shape (recessed shape) in the tomographic image. Owing to this, the image processing unit 108 detects a large recessed region from the tomographic image. Alternatively, if a scanning laser ophthalmoscopy (SLO) image or a fundus picture (a fundus image) is present, the image processing unit 108 may detect a circular optic disk portion from the image, and makes the detected optic disk portion to correspond to the imaging range of the tomographic image. Thus, the image processing unit 108 may detect the optic disk portion from the tomographic image. In a case of horizontal scan at the center of the macula portion, since the optic disk portion is present on the left of the left eye as seen from the front and the optic disk portion is present on the right of the right eye as seen from the front, an end portion (an optic disk portion side) of a tomographic image may be simply determined as an invalid region. In a case of vertical scan at the center of the macula portion, since the optic disk portion is not captured, the processing in this step is not required to be executed.

In step S3034, the image processing unit 108 detects the retina region. To be specific, the image processing unit 108 detects ILM and RPE from the tomographic image, and detects a region arranged between layer boundaries as the retina region. Alternatively, without limiting to the region arranged between ILM and RPE, the image processing unit 108 may detect a region arranged between one of ILM and NFL and one of RPE and a photoreceptor inner segment/outer segment boundary (IS/OS) as the retina region.

Also, since the retina region is brighter than the background region, the image processing unit 108 executes binarization by using a determining and analyzing method, and detects a bright region from the image. The image processing unit 108 executes morphological conversion (closing or opening) and hence connects bright regions, and eliminates a noise portion. The image processing unit 108 obtains the center line for the region, sets an initial boundary line of ILM at a position above the center line and in an upper area (for example, at an upper end) in the region, and sets an initial boundary line of RPE at a position below the center line and in a lower area (for example, at a lower end) in the region. The image processing unit 108 applies an outline extraction algorithm such as Snakes to the boundary lines, and detects the layer boundaries. Snakes defines a shape energy $E_{shape}$ and an image energy $E_{Image}$, and minimizes the energies by repetitive calculation. The shape energy $E_{shape}$ is defined to decrease as the shape of the retina layer becomes smoother, and the image energy $E_{Image}$ is defined to decrease as a portion has a higher edge intensity. The image processing unit 108 finds a portion with the minimum energies while moving all detection points of the boundary lines set with the initial values. Hence, the initial boundary lines are finally output as having layer boundaries (strong edges) and smooth shapes. That is, the image processing unit 108 corresponds to an example of an extracting unit configured to extract a layer boundary from a tomographic image. In the above-described example, the image processing unit 108 extracts ILM (internal limiting membrane) and RPE (retinal pigment epithelium); however, it is not limited thereto. For example, the image processing unit 108 may extract at least one of the internal limiting membrane and the nerve fiber layer boundary, and at least one of the retinal pigment epithelium boundary and the photoreceptor inner segment/outer segment boundary.

In general, since the layer boundary is detected as a smooth boundary line by Snakes, even if a hole is made in the retina layer due to a macular hole, the boundary line of ILM is detected as a smooth boundary line. When the retina thickness is measured, to execute measurement on the basis of boundary line information, the image processing unit 108 may correct the ILM boundary line when a vitreous present region is detected in step S3037 (described later) on the basis of the boundary line of ILM detected here. Alternatively, any one of various known methods may be used for detecting the layer boundary.

In step S3035, the image processing unit 108 normalizes the position of the retina in the depth direction (the Z-direction). To meet a previously set reference image, the position of the retina is normalized by aligning the position in the depth direction of the retina with the position of the retina in the reference image by using the center line obtained in step S3034. The normalization is executed for easier specification of the position when the finding candidate is detected, and for ensuring the place where the finding is displayed in the tomographic image.

In step S3036, the image processing unit 108 detects a candidate region of the macula portion. The macula portion has a small cup shape (recessed shape) in the tomographic image. For example, the cup of the macula portion is smaller than the cup of the optic disk portion. Owing to this, the image processing unit 108 detects a small recessed region from the tomographic image. Alternatively, if a SLO image or a fundus picture (a fundus image) is present, the image processing unit 108 may detect the macula portion from the tomographic image by detecting the macula portion from the image and making the detected macula portion to correspond to the imaging range of the tomographic image. Alternatively, if imaging is executed at the center of the macula portion, since the macula portion is located near the center of the tomographic image, the image processing unit 108 may simply detect an area near the center of the tomographic image as the macula portion. Still alternatively, the image processing unit 108 may detect the macula portion with reference to the position of the optic disk portion detected in step S3033. The ratio of an optic disk diameter (DD) to a distance (DM) from the center of the optic disk to the macular fovea is generally in a range from 2.4 to 3.0. Hence, the image processing unit 108 may use the ratio to roughly specify the macula region.

In step S3037, the image processing unit 108 detects a vitreous present region (an oblique line portion 430 in FIG. 4A). The image processing unit 108 detects a small depth side (an upper side) in the Z-direction of the tomographic image with respect to the retina region (or ILM) detected in step S3034 as a vitreous region. Further, the image processing unit 108 may execute thinning processing in the vitreous region, and extract 405 as a posterior vitreous detachment candidate (see FIG. 5B). Alternatively, the extraction of the posterior vitreous detachment candidate 405 may be executed in step S3038. Now, a case is described, in which the image processing unit 108 corrects ILM after the image processing unit 108 detects the vitreous present region 430. If the macula portion has a hole due to a macular hole, the ILM boundary line detected as the smooth line crosses the vitreous present region 430. Since the vitreous present region 430 is divided by the ILM boundary line, the ILM boundary line may be detected again for the portion.

Then, in step S3038, the image processing unit 108 executes image processing (region extraction for a lesion candidate) on the basis of the image processing parameters respectively corresponding to the plurality of finding candidates. Herein, the image processing parameter "X: 25% to 75%, Z: 30% to 70%, pixel value: 10 or smaller" of "fiber layer cystoid hole" is exemplarily described. In this case, the image processing unit 108 extracts a pixel having a pixel value being 10 or smaller in a rectangular range with X-coordinates in the tomographic image from 25% to 75% and Z-coordinates from 30% to 70%, from the tomographic image normalized by the preprocessing, on the basis of the image processing parameter. Such processing is executed on each of the plurality of finding candidates. The number of tomographic images is one in this embodiment. However, if a plurality of tomographic images are present, the processing is executed on each of the plurality of tomographic images.

The processing returns to step S3040 in FIG. 3A. In step S3040, the determining unit 110 determines whether each of the plurality of finding candidates is a corresponding finding or not (whether each of the plurality of finding candidates is present in the tomographic image or not), on the basis of the plurality of finding candidates acquired in step S3020 and the result of the image processing executed in step S3030.

For example, for "fiber layer cystoid hole," the determining unit 110 recognizes adjacent pixels as a single region in extracted pixels, and calculates the aspect ratio (short side/long side) of each region. Then, for example, the determining unit 110 determines a region with an aspect ratio being 0.7 or smaller as corresponding to "fiber layer cystoid hole." In the case of "posterior vitreous detachment," the determining unit 110 determines a region as corresponding to "posterior vitreous detachment" if the length of a line extracted by the thinning processing is a threshold (for example, 20% of the length of the image in the X-direction) or larger. That is, the image processing unit 108 and the determining unit 110 correspond to an example of a detecting unit configured to detect an abnormal portion of an eye to be inspected by executing structural analysis on a tomographic image acquired by the acquiring unit.

The determination criteria may be stored as part of the second table information, or the storage unit 104 may include as third table information (not shown) storing the determination criteria.

Also, in step S3038, the region with Z-coordinates from 30% to 70% serves as the processing object; however, the region of the processing object may be determined by using the detection result of the layer boundary. For example, the region with Z-coordinates from 30% to 70% may be replaced with the region arranged between ILM and RPE (an example of a first region). That is, to detect the region of the fiber layer cystoid hole (an example of a first abnormal portion), the image processing unit 108 may extract a pixel having a pixel value being 10 or smaller in a range having X-coordinates in the tomographic image from 25% to 75% and arranged between ILM and RPE. Also, as shown in the second table of FIG. 5B, the image processing unit 108 executes the thinning processing in a region located above ILM (an example of a second region) which is the detection result of the layer boundary to detect a region of posterior vitreous detachment (an example of a second abnormal portion). That is, the image processing unit 108 and the determining unit 110 apply structural analysis with different algorithms to the first region and the second region in the tomographic image defined by the layer boundary (for example, ILM) extracted by the extracting unit, to detect the first abnormal portion from the first region and to detect the second abnormal portion different from the first abnormal portion from the second region.

Alternatively, a region arranged between one of the internal limiting membrane and the nerve fiber layer boundary and one of the retinal pigment epithelium boundary and the photoreceptor inner segment/outer segment boundary may serve as the first region. Also, a region on the vitreous body with respect to one of the internal limiting membrane and the nerve fiber layer boundary may serve as the second region. Then, the first abnormal portion and the second abnormal portion may be generated by applying structural analysis with different algorithms to the first region and the second region defined as described above.

Figure 6:
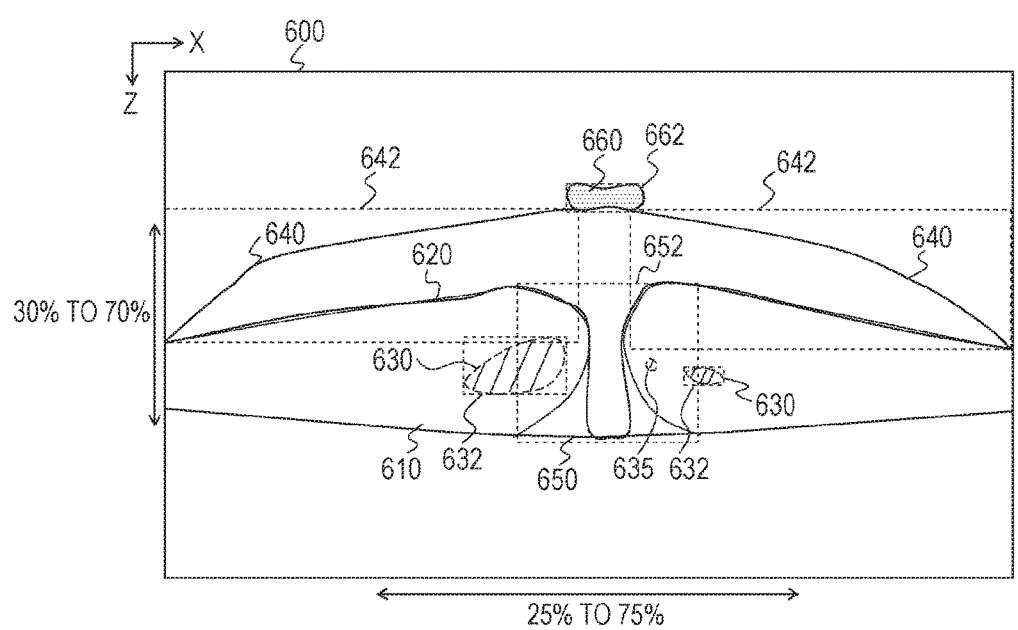
FIG. 6 is an illustration showing an example of image processing and positional specification.

FIG. 6 is an illustration showing an example of the image processing result in step S3030 and an example of the determination result in step S3040. A RPE layer 610 and an ILM 620 shown in FIG. 6 are layer boundaries extracted by the processing in step S3030 from a tomographic image 600.

A region 630 corresponding to the fiber layer cystoid hole and a region 635 not corresponding to the fiber layer cystoid hole indicate regions extracted by using the image processing parameter for "fiber layer cystoid hole" in step S3030. As shown in FIG. 6, the region 630 corresponding to the fiber layer cystoid hole has an aspect ratio being 0.7 or smaller (that is, being horizontally long), and hence the determining unit 110 determines that the region 630 corresponds to "fiber layer cystoid hole." In contrast, the region 635 not corresponding to the fiber layer cystoid hole has an aspect ratio exceeding 0.7, and hence the determining unit 110 determines that the region 635 does not correspond to "fiber layer cystoid hole." Similarly, a region 640 corresponding to posterior vitreous detachment indicates a line extracted by the image processing parameter for "posterior vitreous detachment" in step S3030. In the case of this example, since the length in the X-direction of the line exceeds 20% of the length in the X-direction of the image, the determining unit 110 determines as corresponding to "posterior vitreous detachment." Such determination is made on each of the plurality of finding candidates. In the example in FIG. 6, a macular hole 650 and a lid 660 are determined as corresponding findings in addition to the above-described findings. It is assumed that the finding determined by the computer (the diagnosis support apparatus 100) in this embodiment is referred to as computer-aided diagnosis (CAD) finding.

In step S3050, the position acquiring unit 112 acquires information indicative of a position in the medical image corresponding to the finding (information indicative of the position of a finding) on the basis of the result of the image processing executed in step S3030 and the finding candidate determined as the corresponding finding in step S3040. The information indicative of the position may be any information as long as the information can specify the position. In this embodiment, the position acquiring unit 112 acquires information on a rectangle (for example, four vertex coordinates) including an image region determined as corresponding to the finding, as the information indicative of the position of the finding. In other words, the position acquiring unit 112 acquires information on a rectangle (for example, four vertex coordinates of the rectangle) circumscribing the image region determined as corresponding to the finding, as the information indicative of the position of the finding. The information acquired by the position acquiring unit 112 is not limited to the information on the rectangle including the image region or circumscribing the image region, and the region may have any shape other than the rectangle as long as the region includes the image region.

In the example shown in FIG. 6, the position acquiring unit 112 acquires fiber layer cystoid hole positional information 632 for the region determined as "fiber layer cystoid hole" and posterior vitreous detachment positional information 642 for the region determined as "posterior vitreous detachment" in step S3040. In this case, the fiber layer cystoid hole positional information 632 is positional information on a rectangular region circumscribing the region 630 corresponding to the fiber layer cystoid hole, and the posterior vitreous detachment positional information 642 is positional information on a rectangular region circumscribing the region 640 corresponding to the posterior vitreous detachment.

The position acquiring unit 112 acquires such information indicative of the position of a finding for each of the plurality of determined finding candidates. In the example shown in FIG. 6, macular hole positional information 652 and lid positional information 662 are acquired. Information indicative of the position of the same finding may be acquired for each of respective regions. Alternatively, priorities may be applied to respective regions, and information indicative of a position in a region with the highest priority may be acquired as information indicative of the position of the finding. The priority may be determined with regard to, for example, at least one of the area of the rectangle, the distance from the center of the image, and the distance from an end of the image. For example, if a plurality of the same findings are present in a tomographic image, a high priority is given to a finding with a large rectangular area, and only information indicative of the position of the finding with the large rectangle area among the same findings may be acquired.

In step S3060, the display control unit 116 controls the content to be displayed on the displaying unit 118. Then, the displaying unit 118 displays the display content controlled by the display control unit 116.

To be specific, the display control unit 116 uses the information acquired in step S3050 indicative of the position in the tomographic image of the finding determined as the corresponding finding in step S3040, and causes the information on the finding determined as the corresponding finding to be displayed in a superimposed manner on the tomographic image acquired in step S3000. To be more specific, the display control unit 116 causes the displaying unit 118 to display the tomographic image and to display the finding as a sentence or a word in a superimposed manner. That is, the display control unit 116 corresponds to an example of a display control unit configured to causing the displaying unit to display a finding of an abnormal portion detected by the detecting unit as a sentence or a word in a superimposed manner on a tomographic image. Also, the display control unit 116 causes the finding to be displayed at a position on the tomographic image corresponding to the position of the image region (the abnormal portion) determined as corresponding to the finding.

In this embodiment, it is assumed that the display control unit 116 determines the position of superimposition on the tomographic image under the following display rules for the corresponding finding. (1) Superimposition is not provided on information indicative of a position of another finding determined as the corresponding finding. (2) Character information of a finding is displayed on the lower side in the Z-direction with respect to the RPE layer or on the upper side in the Z-direction with respect to ILM. That is, character information of the finding is not superimposed on the retina. If (3) the information indicative of the position of the finding determined as the corresponding finding is located between the RPE layer and LIM in the Z-direction, a marker (for example, an arrow) is applied to a position near the position of the finding indicated by the information. Of course, the display rules are not limited to the above-described example. For example, the condition (2) may be changed to a condition that the character information of the finding is displayed in a region other than a region arranged between one of the internal limiting membrane and the nerve fiber layer boundary and one of the retinal pigment epithelium boundary and the photoreceptor inner segment/outer segment boundary. Alternatively, the condition (2) may be changed to a condition that at least part of the character information of the finding is displayed on the lower side in the Z-direction with respect to the RPE layer or on the upper side in the Z-direction with respect to ILM. Even if the condition is changed as described above, not all the character information is superimposed on the tomographic image. Accordingly, visibility of the tomographic image can be prevented from decreasing. In the condition (3), in addition to displaying the marker, the character information of the finding may be displayed in a region closer to the image region corresponding to the finding from among the region on the lower side in the Z-direction with respect to the RPE layer and on the upper side in the Z-direction with respect to ILM. Accordingly, a decrease in visibility of the tomographic image due to an unnecessary increase in size of the marker 712 shown in FIG. 7 can be prevented.

Figure 7:
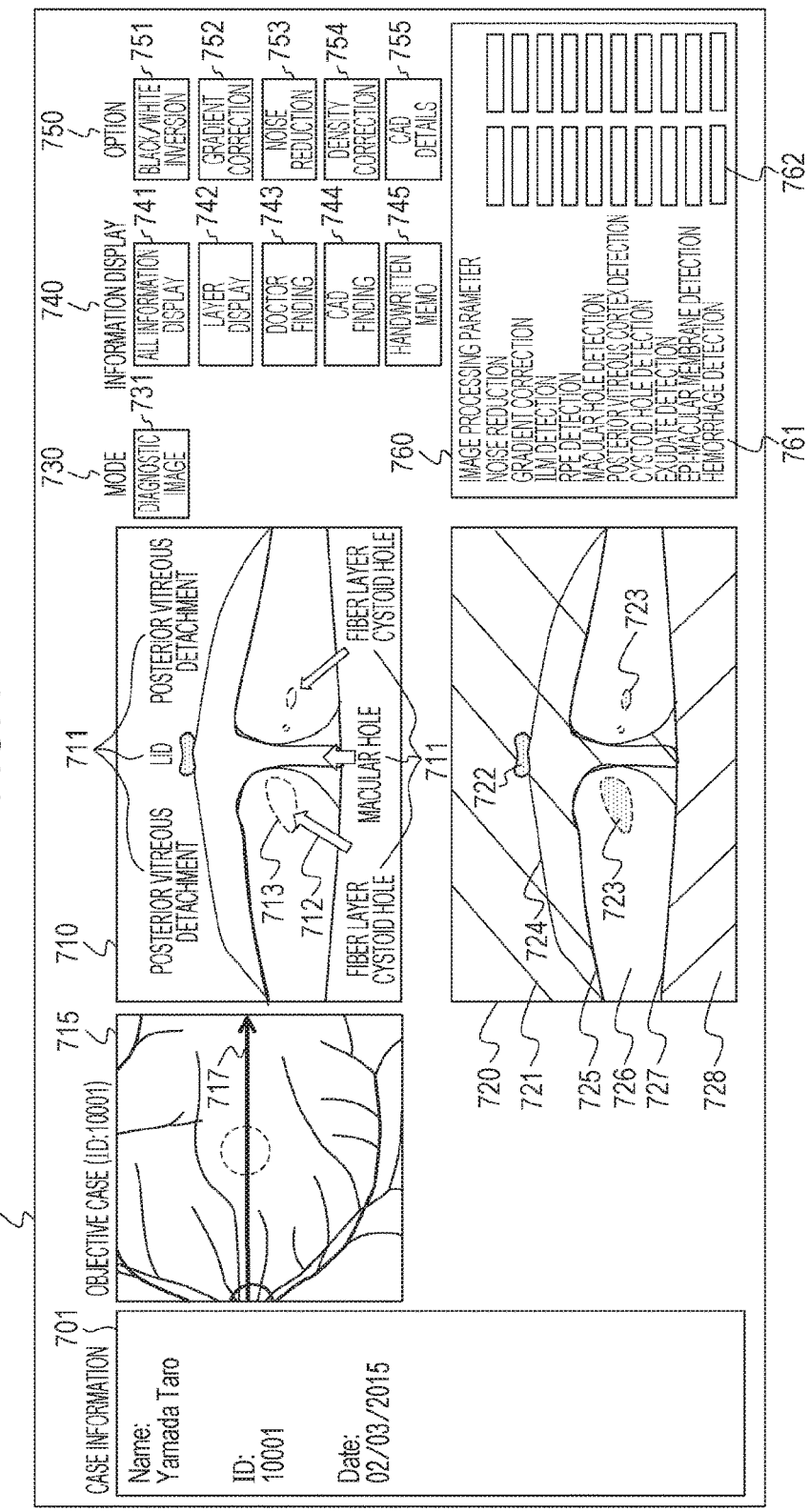
FIG. 7 is an illustration showing an example display of a displaying unit according to a first embodiment.

FIG. 7 illustrates an example of a display content displayed by the displaying unit 118. A display content 700 displayed by the displaying unit 118 includes case information 701, a tomographic image 710 of an objective case, findings 711 superimposed on the tomographic image, a marker 712, a fundus image 715 corresponding to the tomographic image of the objective case, and a horizontal arrow 717 superimposed on the fundus image 715. The horizontal arrow 717 indicates an acquisition position of the tomographic image 710 on the fundus image. Further, the display content 700 includes an analysis processing result image 720, a mode 730, information display 740, an option 750, and an image processing parameter 760.

The display control unit 116 superimposes character information of the findings 711 on the tomographic image on the basis of the above-described display rules and information indicative of the positions of the findings 711. For example, for "fiber layer cystoid hole," information indicative of the position of a region 713 of a fiber layer cystoid hole is located between the RPE layer and ILM in the Z-direction, character information of the finding 711 is displayed on the lower side in the Z-direction with respect to the RPE layer. In this embodiment, the region 713 of the fiber layer cystoid hole is closer to the region on the lower side in the Z-direction with respect to the RPE layer than the region on the upper side in the Z-direction with respect to ILM, the words "fiber layer cystoid hole" are displayed in the region on the lower side in the Z-direction with respect to the RPE layer. Further, the marker 712 is applied to a position near the information indicative of the position of the finding 711. That is, the marker 712 is displayed at a position near the region 713 of the fiber layer cystoid hole being an abnormal portion. Also, for "posterior vitreous detachment," information indicative of the position of "posterior vitreous detachment" is located on the upper side in the Z-direction with respect to ILM, and hence character information of the finding 711 is displayed at a position near information indicative of the position of "posterior vitreous detachment" so that the character information does not overlap ILM. In the example shown in FIG. 7, the character information of the finding 711 is displayed so that the character information does not overlap the detected vitreous detachment. Alternatively, the character information of the finding 711 may be displayed so that at least part of the character information does not overlap the detected vitreous detachment.

Similarly to the above-described processing, for "macular hole" and "lid," character information of the finding 711 is displayed at a position near an abnormal portion. The character information of the finding 711 to be displayed may be words like "posterior vitreous detachment," or may be a sentence "detachment is present at posterior vitreous body."

The analysis processing result image 720 is an image indicative of the above-described image analysis result. The analysis processing result image 720 indicates a vitreous body region 721 (an oblique line portion), a lid 722, a fiber layer cystoid hole 723, posterior vitreous detachment 724, ILM 725, a retina layer region 726, RPE 727, and a subchoroidal region 728. These indicate the analysis results of image analysis on the tomographic image being the basis for outputting the findings 711. In this embodiment, the example is described, in which the lid 722, the fiber layer cystoid hole 723, and the posterior vitreous detachment 724 are detected as lesion portions (abnormal portions); however, it is not limited thereto. If an epi-macular membrane, retinal atrophy, hard exudate, etc., are present, the detection results of these are indicated. The analysis processing result image 720 may be displayed and may not be displayed.

The mode 730 indicates a display mode. In this embodiment, a mode of displaying a finding on a tomographic image is used as a diagnostic image mode 731. In embodiments (described later, FIGS. 11 and 14), an interface that can select one of a plurality of modes is displayed as the mode 730.

The information display 740 is a user interface for selecting information displayed on the tomographic image. A user such as a doctor can change information to be displayed on the tomographic image, for example, by clicking or tapping the displayed user interface. As the user interface, diagnostic image display (all information display) 741 is displayed on the displaying unit 118. The diagnostic image display 741 turns ON/OFF superimposition of all information, such as the layer detection result, a finding by a doctor, a finding by CAD, and a handwritten memo on the tomographic image 710. Further, as the user interface, in order to individually switch information to be superimposed, layer detection display (layer display) 742 is displayed on the displaying unit 118. The layer detection display 742 turns ON/OFF display of a layer detection result. In addition, doctor finding display 743 to turn ON/OFF display of a finding confirmed by a doctor is displayed on the displaying unit 118. As the user interfaces, CAD finding display 744 to turn ON/OFF display of a finding detected by CAD, and handwritten memo display 745 to turn ON/OFF display of a handwritten memo are displayed on the displaying unit 118. The user interface for designating the information display 740 is, for example, a button or a checkbox.

The finding includes not only the CAD finding but also the finding confirmed by the doctor. The CAD finding indicates a finding determined by the computer. The finding by the doctor indicates a finding output from the computer and confirmed (approved) by the doctor or a finding detected by CAD and corrected by the doctor. Also, the finding may include a finding newly added by the doctor. To confirm a CAD finding, a CAD finding can be confirmed by an operator such as a doctor selecting an approval checkbox (not shown) or the like. In this case, a plurality of CAD findings may be collectively confirmed. With use of a PC device having a mouse, a CAD finding can be confirmed by selecting the CAD finding by clicking a checkbox. For example, the checkbox is displayed near each of the findings 711. Also, with use of a touch panel monitor, the CAD finding can be confirmed by selecting the CAD finding by tapping a screen. To collectively confirm findings, the findings may be collectively confirmed by double clicking or double tapping a position on the tomographic image 710 not occupied by the findings 711. For a method of correcting a CAD finding, a doctor or the like may select a predetermined finding 711 by tapping or clicking the finding 711 displayed on the displaying unit 118, and correct the selected finding 711 by using the keyboard 1007 or the like.

Also, the findings 711 may be individually selected and confirmed. In this case, a menu may be displayed by right-clicking on a finding, and "confirm" included in the menu may be selected. Alternatively, a finding 711 may be double-clicked or double-tapped to be confirmed. Further, a finding 711 may be temporarily selected by touching, and the finding 711 may be confirmed by making a slide gesture (swiping) on the touch panel monitor in the temporarily selected state. To correct a finding, when a finding 711 is selected, other finding names are displayed near the finding 711 as a list box, and a desirable one of the findings may be selected and confirmed. To delete an unnecessary finding, a finding 711 may be selected and delete may be selected from the menu, or the finding 711 may be dragged to the outside of the tomographic image 710 and deleted. That is, the display control unit 116 can detect an operation on the finding 711 and delete the finding 711 from the display screen.

Also, a confirmation cancel function is also provided for collective confirmation and individual confirmation of findings. In case of the checkbox, the checkbox may be unchecked. In case of double-click or double-tap, confirmation may be canceled by executing the same operation again.

Since the findings include the finding confirmed by the doctor, it is desirable to display the finding confirmed by the doctor with a different color of characters from the color of characters of the finding determined by the CAD (the diagnosis support apparatus 100). For example, the CAD finding may use red, and the doctor finding may use blue. Accordingly, whether the finding is by the CAD or the doctor can be easily recognized at a glance. Without limiting to the color of characters, display in any form may be provided as long as display provides a difference between a CAD finding and a doctor finding, for example, by adding an icon, surrounding a word with a rectangle, adding a shade to characters, or changing the font of characters. For example, if the display control unit 116 receives correction on a CAD finding by a doctor input through the keyboard 1007 or the like, the display control unit 116 may display the finding 711 in a different display form between the finding 711 before the correction and the finding 711 after the correction by the doctor. For example, the display control unit 116 changes the color of characters of the finding 711 between the finding 711 before the correction and the finding 711 after the correction. That is, the display control unit 116 corresponds to an example of a receiving unit configured to be displayed on the displaying unit by an operator and receive correction on a finding. The display control unit 116 causes the displaying unit to display the corrected finding in a display form different from that of the finding before the correction.

The time point at which the display control unit 116 changes the color of characters may be immediately after the change is made by the doctor, or may be a time point at which the correction is confirmed by selecting an approval checkbox or the like (not shown).

Further, the display control unit 116 may control the displaying unit 118 to display the finding 711 after changing the color of characters of the finding 711 in accordance with the type of finding. In this case, the icon, font, etc., is changed between the finding by the CAD and the finding by the doctor, and the same color is applied to the same finding. For example, the macular hole uses light blue, and the lid uses purple. The finding by the CAD uses oblique style, and the finding by the doctor uses thick font.

Also, a desirable comment may be written as a handwritten memo in addition to the finding. The difference between the handwritten memo and the finding input is described below. When characters are input, a select portion for selecting whether handwritten memo input or finding input (not shown) may be provided, and the CPU 1001 may determine whether the input is the handwritten memo input or the finding input on the basis of selection by the doctor. Alternatively, a word of the finding may be selected and added from a previously registered finding dictionary in the case of the finding input, and free input may serve as a handwritten memo. Still alternatively, the characters of the input word are analyzed, and the word registered in the finding dictionary is determined as a finding. Further alternatively, a finding obtained by correcting the finding output from the CAD, or a finding obtained by a doctor confirming the finding output from the CAD may serve as a finding, and free input may serve as a handwritten memo.

The option 750 is a user interface for executing processing on the tomographic image or displaying information on the CAD. A user such as a doctor may execute the processing on the tomographic image by the image processing unit 108 or display the information on the CAD by the display control unit 116, for example, by clicking or tapping the displayed user interface. As the option 750, user interfaces, such as black/white inversion display 751, gradient correction display 752, noise reduction 753, density correction 754, and CAD details 755, are displayed. The black/white inversion display 751 for designating black/white inversion of the displayed image is a user interface for switching display between display that the display color of a low reflection region in the tomographic image is black and the display color of a high reflection region is white and display that the display color of a low reflection region is white and the display color of a high reflection region is black. The gradient correction display 752 is a user interface for correcting the gradient of the retina layer. The gradient correction display 752 corrects the gradient of the retina layer to be displayed on the basis of the image processing parameter 760. The noise reduction 753 is a user interface for reducing a noise from the tomographic image on the basis of the image processing parameter 760. The density correction 754 is a user interface for correcting window width/window level (WW/WL) of the tomographic image. The CAD details 755 is a user interface for selecting ON/OFF of display of the analysis processing result image 720 and the image processing parameter 760. That is, the analysis processing result image 720 and the image processing parameter 760 are displayed on the displaying unit 118 by the display control unit 116 when the CAD details 755 is selected. Also, the analysis processing result image 720 may display an in-progress result during execution of the analysis processing. The window of the image processing parameter 760 displays parameter items 761 required for image processing and their numerical values 762. The processing is executed on the basis of the displayed numerical values. The numerical values 762 may be edited by using the mouse 1006, the keyboard 1007, or the like.

Figure 8:
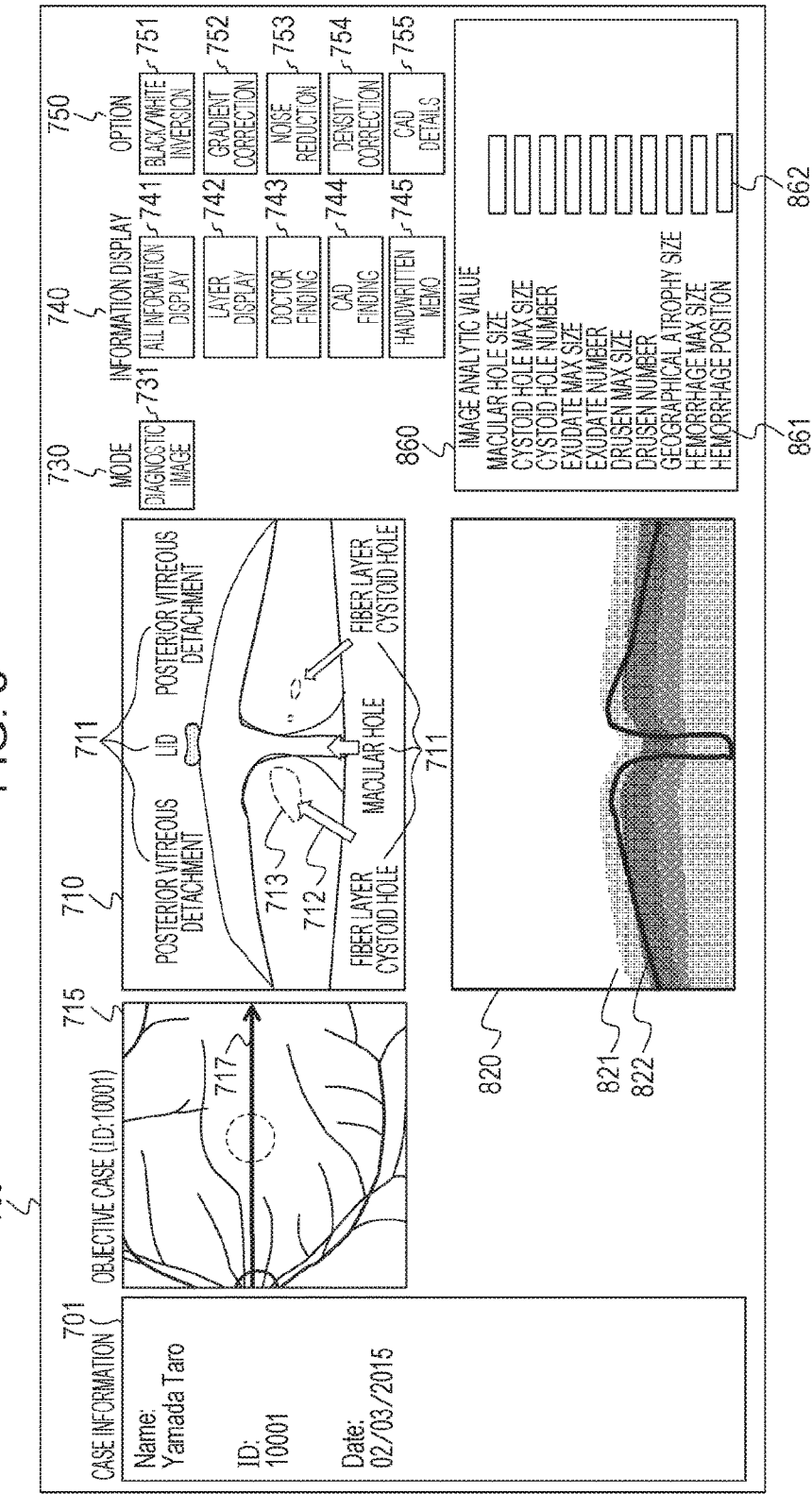
FIG. 8 is an illustration showing an example display of the displaying unit according to the first embodiment.

FIG. 8 illustrates another display example according to this embodiment. In FIG. 8, analytic data 820 and an analytic value 860 are displayed instead of the analysis processing result image 720 and the image processing parameter 760 in FIG. 7. Other display is the same as the example shown in FIG. 7. The display is switched by turning ON/OFF the CAD details 755. The ON state of the CAD details 755 is a default state in the diagnostic image mode 731. However, the OFF state of the CAD details 755 may be a default state and display of the analytic data 820 and the analytic value 860 may be default by setting (not shown). The analytic data 820 indicates a statistical normal eye database 821 and a layer thickness graph 822 of the displayed tomographic image 710. For example, the normal eye database 821 is color-coded for a range "outside the upper limit of normal values" (99% or higher), a range on "upper-side boundary line" (95% to 99%), a range of "normal values" (5% to 95%), a range on "lower-side boundary line" (1% to 5%), and a range "outside the lower limit of normal values" (1% or lower). The layer thickness graph 822 can provide a view relating to a range of the retina layer outside normal values by comparison with the normal eye database 821. The image analytic value 860 is the result of measurement on the size and number of determined lesions, on the basis of the image processing in step S3030 and the determination result for the finding candidate in step S3040.

With this embodiment, the diagnosis support apparatus 100 acquires a corresponding finding candidate and an image processing parameter relating to derivation of the finding candidate on the basis of information on a portion of a medical image. Then, the diagnosis support apparatus 100 executes image processing on the basis of the acquired image processing parameter, determines the corresponding finding and specifies the position, and provides these results. Accordingly, a doctor can recognize the finding determined as the corresponding finding and its position on the medical image, and the analysis result. Accordingly, since the doctor can view the state of the medical image being a current object and the diagnostic name, the burden on diagnosis can be decreased.

To be more specific, with this embodiment, since the finding is displayed on the tomographic image, the doctor or the like can easily recognize the relationship between the tomographic image and the finding. Also, since the finding is displayed depending on the position of an abnormal portion in the tomographic image, the doctor or the like can easily recognize the relationship between the abnormal portion and the finding, and can quickly make a diagnosis.

Further, since the finding is displayed not to overlap the retina region in the tomographic image as possible, the finding can be displayed on the tomographic image while preventing a decrease in visibility of the tomographic image itself.

Second Embodiment

In the first embodiment, the medical image being the diagnosis object is acquired, the support information such as the CAD finding is provided on the medical image by using the image processing result, and the analytic image and the analytic data of the image processing are provided. Described in this embodiment are provision of support information on a medical image and provision of a result of a similar case (a similar image).

An example of a functional configuration of a diagnosis support apparatus 900 according to a second embodiment is described with reference to FIG. 9. As compared with FIG. 1, a searching unit 914 and a database 300 are functionally added to the diagnosis support apparatus 900. The database 300 is connected with the diagnosis support apparatus 900 in a wired or wireless manner to enable communication therebetween. The database 300 stores a medical image, and a finding and a diagnostic name corresponding to the image in an associated manner. That is, the database 300 corresponds to an example of a storage unit configured to store a plurality of tomographic images in association with respective findings.

Also, the medical image stored in the database 300 is associated with patient information, such as the sex and age. In response to a request from the diagnosis support apparatus 900, the database 300 outputs the medical image and the finding corresponding to the request to the diagnosis support apparatus 900. Alternatively, the database 300 may be stored in the storage unit 104 in the diagnosis support apparatus 900. The searching unit 914 requests for information on an image similar to the objective medical image from the database 300, by using a finding candidate determined as the corresponding finding by the determining unit 110 as a key. The searching unit 914 receives the requesting information from the database 300. The searching unit 914 outputs the received information on the image together with the similarity to the objective medical image to the display control unit 116. The diagnosis support apparatus 900 has a similar hardware configuration to that in FIGS. 2A and 2B according to the first embodiment. That is, the CPU 1001 executes the programs stored in the main memory 1002 and the magnetic disk 1003, and hence realizes the functions (the software) of the diagnosis support apparatus 900 and processing in a flowchart according to this embodiment.

Figure 10:
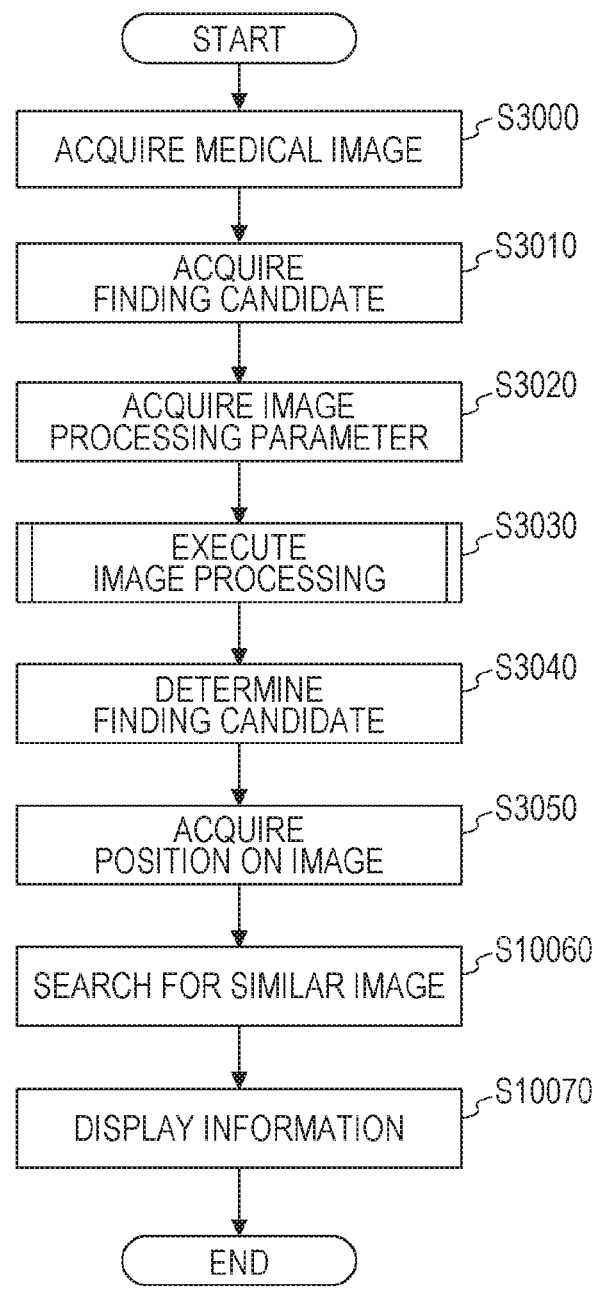
FIG. 10 is a flowchart showing an example of processing of the medical diagnosis support apparatus.

FIG. 10 shows a flowchart for describing an example of processing executed by the diagnosis support apparatus 900. This flowchart is basically similar to the flow in FIG. 3A according to the first embodiment; however, part of the processing differs from the first embodiment. To be specific, this flowchart differs from the flow in FIG. 3A for search of a similar image (S10060) and display of information (S10070). For processing executed by the diagnosis support apparatus 900 according to this embodiment, only part different from the first embodiment is described below with reference to the flowchart in FIG. 10 and an example of a display content in FIG. 11.

In the flowchart in FIG. 10, processing from step S3000 to step S3050 is similar to the processing according to the first embodiment. Hence, the description is omitted.

In step S10060, the searching unit 914 acquires a similar image from the database 300 by using the finding candidate determined as the corresponding finding in step S3040 as a key. That is, the searching unit 914 corresponds to an example of a similar image acquiring unit configured to acquire a tomographic image associated with a finding matched to a finding of an abnormal portion detected by the detecting unit, from the storage unit.

The search key is, for example, "posterior vitreous detachment" or "macular hole." The number of findings each serving as a search key may be plural or one. The finding stored in the database 300 is, for example, a finding previously specified by a doctor for a case. It is assumed that the database 300 also includes information relating to the position of the finding specified by the doctor. Instead of the information previously specified by the doctor, the information on the finding included in the database 300 may be document information such as a textbook, or may be information on a finding specified by a doctor for a case collected for the database.

The method of acquiring a similar image by the searching unit 914 may be acquiring only a similar image with a completely matched search key from the database 300, or may be acquiring a similar image with a partly matched search key. For example, if a plurality of findings serve as search keys, the searching unit 914 may acquire a similar image matched to only part of a plurality of findings. Alternatively, the similarity may be calculated by a certain method, and images may be acquired by a predetermined number in the descending order of similarity. In this embodiment, it is assumed that only an image with a completely matched search key is acquired. The method using the similarity is described later as a modification.

In step S10070, the display control unit 116 controls the content to be displayed on the displaying unit 118. Then, the displaying unit 118 displays the display content controlled by the display control unit 116. To be specific, the display control unit 116 uses the information acquired in step S3050 indicative of the position in the medical image with the finding determined as the corresponding finding in step S3040, and causes the information on the finding determined as the corresponding finding to be superimposed on the medical image acquired in step S3000. The display rules for the findings information is similar to those of the first embodiment. Further, the display control unit 116 causes a similar image and information on a diagnostic name associated with the similar image to be displayed in the descending order of similarity on the basis of the information on the similar image acquired in step S10060. In this embodiment, since only the image with the completely matched key is acquired in step S10060, regarding the patient information relating to the medical image acquired in step S3000, a similar image of the same sex and close age is displayed first. Alternatively, if information relating to life habit can be acquired in addition to the imaging information, an item of life habit may be added to the search key. For example, the search may be executed by using information on whether the patient gets diabetes or not, or whether the patient smokes or not. Also, information captured on the latest date may be displayed first. Also, in this embodiment, the similar image and the information on the diagnostic name associated therewith are managed in a list, information on the list is displayed, and one of cases in the list is displayed in a manner comparable with the medical image acquired in step S3000. The one case displayed in a comparable manner may be selected by the diagnosis support apparatus 900, or the diagnosis support apparatus 900 may receive selection by a user input. For example, a list box storing a list of similar cases may be prepared as a user interface, and one case may be selected from the list box.

In this embodiment, it is assumed that the display control unit 116 determines a similar image captured on the latest date as an initial one case displayed in a comparable manner, and thereafter, the display control unit 116 determines a case displayed in a comparable manner in accordance with selection by a user input. The displaying method is not limited thereto. For example, a plurality of similar images and information on diagnostic names associated therewith may be displayed in a comparable manner with the medical image acquired in step S3000, or all similar images may be displayed in a comparable manner.

Figure 11:
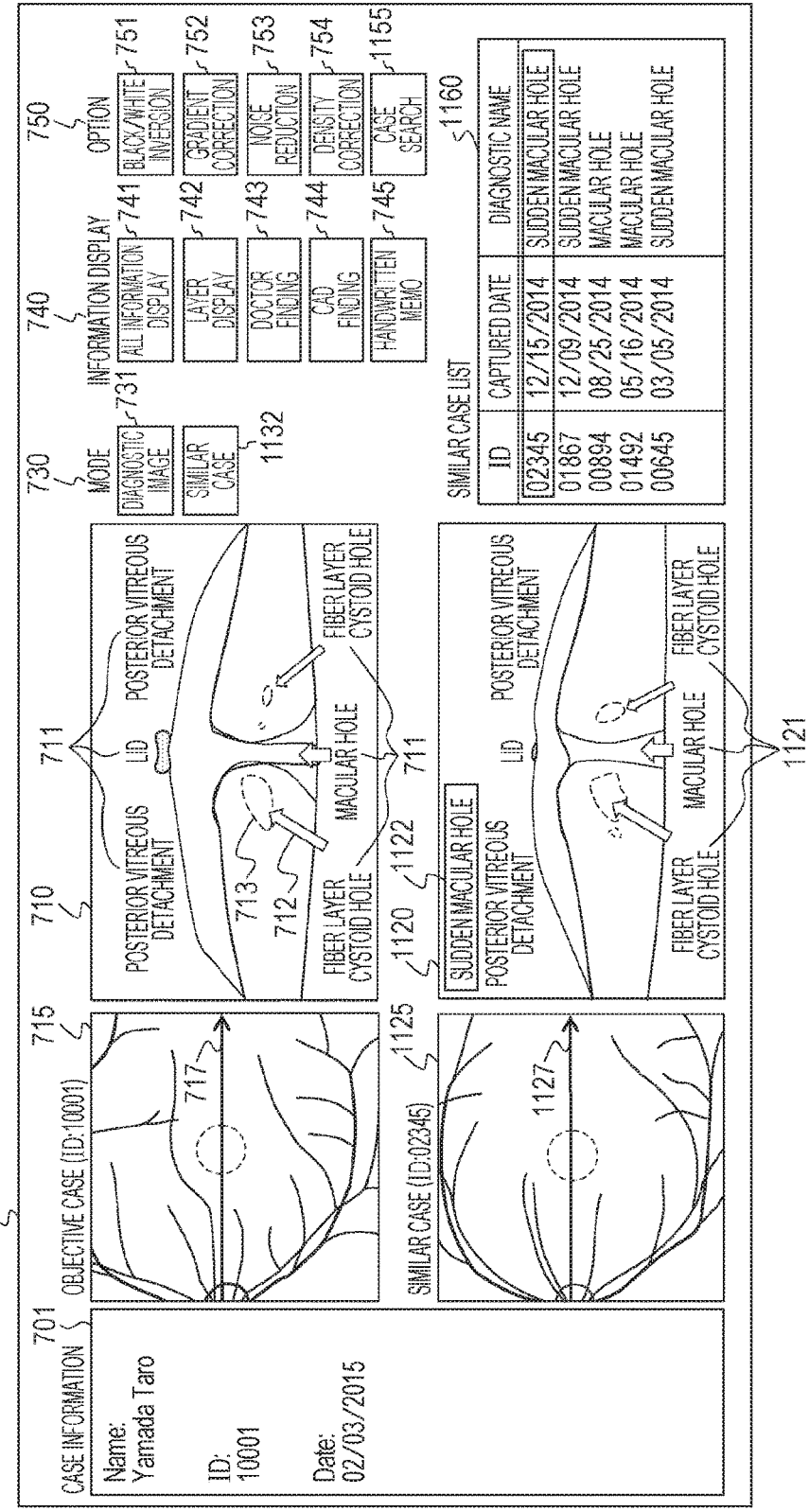
FIG. 11 is an illustration showing an example display of a displaying unit according to a second embodiment.

FIG. 11 illustrates an example of a display content displayed by the displaying unit 118. The display content 700 displayed by the displaying unit 118 is based on the illustration described with reference to FIG. 7 in the first embodiment. The second embodiment differs from the first embodiment in that a similar case mode 1132 is displayed as a user interface. If the similar case mode is selected by a doctor or the like tapping or clicking the similar case mode 1132, the display control unit 116 causes a similar case list (that is, a list in which similar images are displayed in the descending order of similarity) 1160 to be displayed. The display control unit 116 causes the displaying unit 118 to display a tomographic image 1120 of one case in the similar case list (in this case, an image captured on the latest date as described above), a finding 1121, a diagnostic name 1122, and a fundus image 1125 corresponding to the tomographic image. If the similar case mode 1132 is selected, a case search 1155 being a user interface for executing case search is added to the option 750. The search for a case similar to the objective tomographic image 710 is executed by an operator such as a doctor tapping or clicking the case search 1155. In this embodiment, the example is described in which the user interface for executing the case search is different from the similar case mode 1132; however, the case search may be executed simultaneously when the similar case mode 1132 is selected.

In the tomographic images 710 and 1120 with findings superimposed, the information on the findings 711 and 1121, which are determined as the corresponding findings on the basis of the information indicative of the positions of the findings, is superimposed under the above-described display rules. As described above, if another case in the similar case list is determined as a case to be displayed in a comparable manner as the result of selection by a user input, the display control unit 116 controls the display content of the displaying unit 118. To be specific, the display control unit 116 causes the displaying unit 118 to display the tomographic image 1120 with the findings superimposed, the diagnostic name 1122, and the fundus image 1125 corresponding to the tomographic image, which correspond to the case selected in the similar case list 1160.

With this embodiment, the diagnosis support apparatus 900 acquires a corresponding finding candidate and an image processing parameter relating to derivation of the finding candidate on the basis of information on a portion of a medical image. Then, the diagnosis support apparatus 900 executes image processing in accordance with the acquired image processing parameter, determines the corresponding finding and specifies the position, searches for a similar image on the basis of the finding determined as the corresponding finding, and provides these results. Accordingly, the doctor can recognize the finding determined as the corresponding finding and its position on the medical image, and the diagnostic name associated with the similar image. Accordingly, since the doctor can view the state of the medical image being a current object and the diagnostic name of the similar case, the burden on diagnosis can be decreased.

Also, in a default state, the image with the most similar to the medical image being the current object is displayed in a comparable manner, and hence an operator such as a doctor can save the time required for selecting an image suitable for comparison.

The information stored in the database 300 is not limited to the above-described example. For example, the database 300 may store the medical image; the finding and diagnostic name corresponding to the image; and the position, the diagnostic name, and the finding in the tomographic image with the corresponding finding in an associated manner. In this case, the searching unit 914 can search for a similar image by using the finding and the position of the finding as search keys. For example, the searching unit 914 may acquire a tomographic image (a similar image) in which the finding is matched, and the position of the finding is matched, or the difference between the position of the finding in the objective tomographic image and the position of the finding in the tomographic image in the database 300 is a predetermined threshold or smaller, from the database 300. That is, the database 300 may store each of a plurality of tomographic images in association with a finding and the position in the tomographic image with the finding. Also, the searching unit 914 being an example of the similar image acquiring unit acquires a tomographic image associated with a finding and a position of the finding matched to a finding and a position of the finding of an abnormal portion detected by the detecting unit.

Accordingly, the similar image with the matched finding and the matched position of the finding can be acquired. A tomographic image having symptoms closer to an objective tomographic image can be acquired.

First Modification

Figure 12:
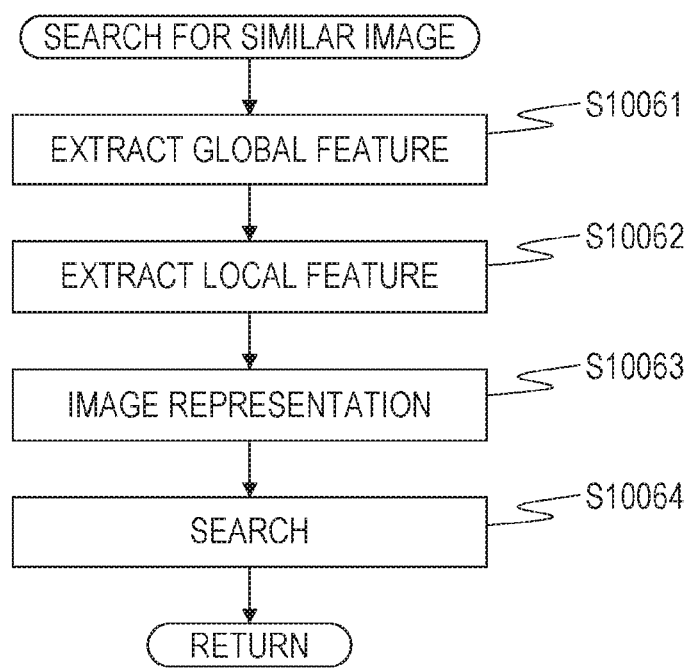
FIG. 12 is a flowchart showing an example of processing of the medical diagnosis support apparatus.

In the above-described embodiment, a similar case with a matched finding is searched by using a finding as a search key. However, the method of similar case search is not limited thereto. For example, a similar case may be searched on the basis of an image feature value. This processing is described with reference to a flowchart in FIG. 12. FIG. 12 illustrates the details of the processing in step S10060 in the flowchart of FIG. 10.

In step S10061, the image processing unit 108 extracts a thickness feature of a retina layer from a tomographic image as global feature extraction. For the thickness of the retina layer, it is assumed that the difference in the Z-direction between ILM and the boundary line of RPE serves as the thickness of the retina layer. As a region for calculating the thickness of the retina layer, the image processing unit 108 extracts feature values from a macula portion center region, left and right regions excluding the center of the macula portion, and the entire region. As a method of dividing the region, the tomographic image may be simply divided into three sections in the X-direction, or may be divided into five sections, the left and right regions may take ⅖ each, and the macula region may take ⅕ at the center. When the thickness is calculated, the optic disk region is desirably removed from the region for calculating the thickness. The feature value of the thickness in each region may be one of an average thickness, a maximum thickness, a minimum thickness, a dispersion, or a standard deviation. The image processing unit 108 creates a global feature vector from these feature values. As described above, the global feature represents the shape feature of the entire retina.

In step S10062, the image processing unit 108 calculates a histogram of oriented gradients (HOG) feature in a local region in the retinal inner layer as local feature extraction. The HOG feature is a feature value for calculating the gradient orientation and the gradient intensity of the luminance in a local region, and creating a histogram with the horizontal axis plotting the gradient orientation and the vertical axis plotting the gradient intensity. If the retina inner layer is normal, the retina inner layer has a layer structure. Hence, the gradient orientation of the luminance is aligned in the local region. However, if the layer structure is disordered by a lesion, the gradient orientation of the luminance is also disordered. In this way, the local feature represents the arrangement state of layers in the retina inner layer. The region where the HOG feature is calculated is not the entire tomographic image of OCT, and is desirably the retina region described in step S3034 according to the first embodiment. The local feature value to be obtained in this case is several thousands of dimensions, and therefore, the number of dimensions is decreased by image representation (described later).

In step S10063, the image processing unit 108 converts the local feature value obtained in step S10062 into image representation by Bag of Features. Bag of Features is a method of classifying images in accordance with the frequency of emergence of an image feature registered in the dictionary of image feature values (codebook). During learning, local feature values are extracted from all leaning images, clustering is executed on the extracted local feature values in a feature space, and the center of gravity of each cluster serves as Visual word (codebook). Clustering at this time uses K-means. At image representation in step S10063, the image processing unit 108 votes the local feature value obtained in step S10062 to Visual word being the closest to Visual word created during learning. Accordingly, the image processing unit 108 converts the local feature value into the local feature vector counting the frequency of emergence of Visual word.

In search in step S10064, the searching unit 914 searches for a similar image by using the global feature vector obtained in step S10061 and the local feature vector obtained in step S10063. A searching method may be calculating the similarities of the global feature vector and the local feature vector, and provides the search result by using the total similarity. The similarity may be, for example, cosine similarity. A cosign similarity is provided by Expression (1) as follows:

$$\cos(\vec{V}_t, \vec{V}_s) = \frac{\vec{V}_t \cdot \vec{V}}{|\vec{V}_t||\vec{V}|}, \quad (1)$$

where $V_t$ is an image feature vector being an object, and $V_s$ is an image feature vector stored in the database 300.

As the similarity is closer to 1, the two vectors are more similar to each other. As the similarity is closer to 0, the two vectors are not similar.

The method of calculating the similarity is not limited thereto, and a deviation pattern similarity may be calculated. The deviation from an average value in a group to which each element belongs represents a similarity, and the maximum value is 1. That is, the deviation pattern similarity is the similarity reflecting the distribution of data in the feature space. If such a similarity is used, display is desirably provided in the case list in the descending order of similarity in step S10070. As described above, the similar case can be searched on the basis of the image feature value, instead of the search based on the finding.

The database 300 may store each of a plurality of tomographic images in association with a finding, information based on the thickness of a predetermined layer in the tomographic image, and information based on the luminance of the retina included in the tomographic image. In this case, the information based on the thickness of the predetermined layer in the tomographic image is, for example, a global feature vector, and the information based on the luminance of the retina included in the tomographic image is, for example, a local feature vector. If the database 300 stores the aforementioned information, the searching unit 914 acquires a tomographic image associated with a finding of an abnormal portion, information based on the thickness of the layer, and information based on the luminance corresponding to a finding of an abnormal portion detected by the detecting unit, information based on the thickness of the layer, and information based on the luminance, from the storage unit. This modification may be applied to any other embodiment without limiting to the second embodiment.

Second Modification

In the second embodiment, in step S3060, the searching unit 914 acquires only the image (the case) with the completely matched search key by using the finding candidate determined as the corresponding finding in step S3040 as the search key from the database 300. However, an image with a partly matched search key may be acquired, or an image may be acquired by using a method of calculating the similarity of search keys.

For the similarity, for example, cosign similarity by calculation of vector similarity can be used. Specific description is given below. First, the image processing unit 108 creates a finding vector by using the plurality of finding candidates acquired in step S3010 and the finding candidate determined as the corresponding finding in step S3040. The finding vector can be generated by treating each finding candidate as an element of a vector, and giving 1 if a finding candidate corresponds to a finding in an objective image, and giving 0 if not. For example, if 20 finding candidates are present, a 20-dimensional finding vector is provided. Then, the image processing unit 108 generates a finding vector that is generated as described above and a finding vector of the medical image stored in the database 300. The searching unit 914 calculates the similarity of these vectors. Alternatively, the database 300 may previously store a finding vector.

When $V_t$ is the finding vector of the objective medical image and $V_s$ is the finding vector of the medical image stored in the database 300, the cosign similarity is shown by Expression (1) described according to the first modification.

This modification may be applied to any other embodiment without limiting to the second embodiment. A similar case may be searched by using both the similarity in image feature described in the first modification and the similarity in finding. To be specific, since the similarities each are normalized by 1, the total sum of the similarities may simply represent the final similarity, or the final similarity may be calculated by adding respective waits to the image feature similarity and the finding similarity.

Third Modification

In the second embodiment, the doctor previously specifies the corresponding finding and the position of the finding of the case stored in the database 300. However, the finding may be specified by another method. For example, the processing from step S3010 to step S3050 may be executed on the case stored in the database 300, and the corresponding finding and the positional information on the finding may be associated with the medical image. Also, after the processing in step S10070 is executed, the corresponding case may be stored in the database.

Fourth Modification

In the second embodiment, the searching unit 914 searches for the similar case from the cases stored in the database 300. However, the similar case is not necessarily searched from the externally connected database 300. For example, case information having information equivalent to the database 300 may be stored in the storage unit 104, and the searching unit 914 may search for a similar case from the case information stored in the storage unit 104. In this case, the case information stored in the storage unit 104 may be switched in accordance with various conditions, such as a user, an installation position, and a time. Similarly, the first table information and the second table information may be switched in accordance with the conditions.

Third Embodiment

In the second embodiment, the medical image being the diagnosis object is acquired, the support information is provided on the medical image by using the image processing result, and the analytic image of the image processing and the similar case are provided. In this embodiment, an example is described in which support information such as a CAD finding is provided on a medical image, and information serving as a guideline is provided for a diagnosis. The guideline according to this embodiment is information for support of a diagnosis. The guideline includes information in text or figures, such as a diagnosis manual indicative of a diagnosis procedure, an atlas, a radiogram inspection point, an image of the same modality, and an image of a different modality (for example, a fundus picture, a fluorescein angiography (FA) image, an indocyanine green angiography (IA) image, or the like). That is, the guideline is information indicative of the diagnosis procedure for a disease. Also, the database 300 stores a plurality of guidelines. That is, the database 300 stores information indicative of diagnosis procedures of a plurality of diseases. The guideline may be an electronic book.

Figure 9:
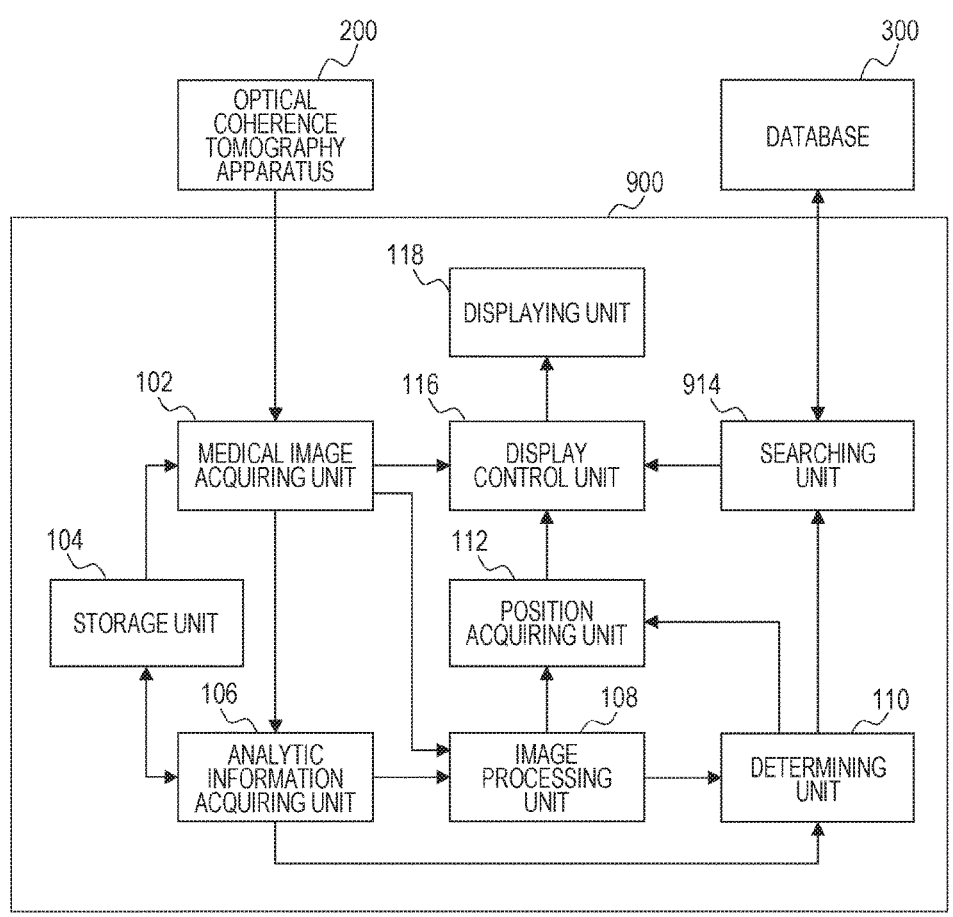
FIG. 9 is an illustration showing an example of a functional configuration of a medical diagnosis support apparatus.

A functional configuration of a diagnosis support apparatus 900 according to this embodiment is similar to that in FIG. 9 according to the second embodiment. The database 300 stores a medical image, and a guideline and a finding corresponding to the image in an associated manner. That is, the database 300 stores information indicative of diagnosis procedures of a plurality of diseases in association with respective findings. In response to a request from the diagnosis support apparatus 900, the database 300 outputs the guideline and the finding corresponding to the request, to the diagnosis support apparatus 900. Alternatively, the database 300 may be stored in the storage unit 104 in the diagnosis support apparatus 900. The searching unit 914 requests for a guideline corresponding to the objective medical image from the database 300, by using a finding candidate determined as the corresponding finding by the determining unit 110 as a search key. Then, the searching unit 914 receives (acquires) the guideline from the database 300. That is, the searching unit 914 corresponds to an example of an information acquiring unit configured to acquire information indicative of a diagnosis procedure of at least one disease from information indicative of diagnosis procedures of a plurality of diseases on the basis of a finding of an abnormal portion detected by the detecting unit. To be specific, the searching unit 914 being the example of the information acquiring unit acquires information indicative of a diagnosis procedure of a disease associated with a finding of an abnormal portion detected by the detecting unit.

Further, the searching unit 914 outputs the received guideline together with the association degree with an objective medical image to the display control unit 116. Then, the display control unit 116 causes the displaying unit 118 to display the guideline. That is, the display control unit 116 causes the displaying unit to display the information indicative of the diagnosis procedure of the disease acquired by the information acquiring unit.

Figure 13:
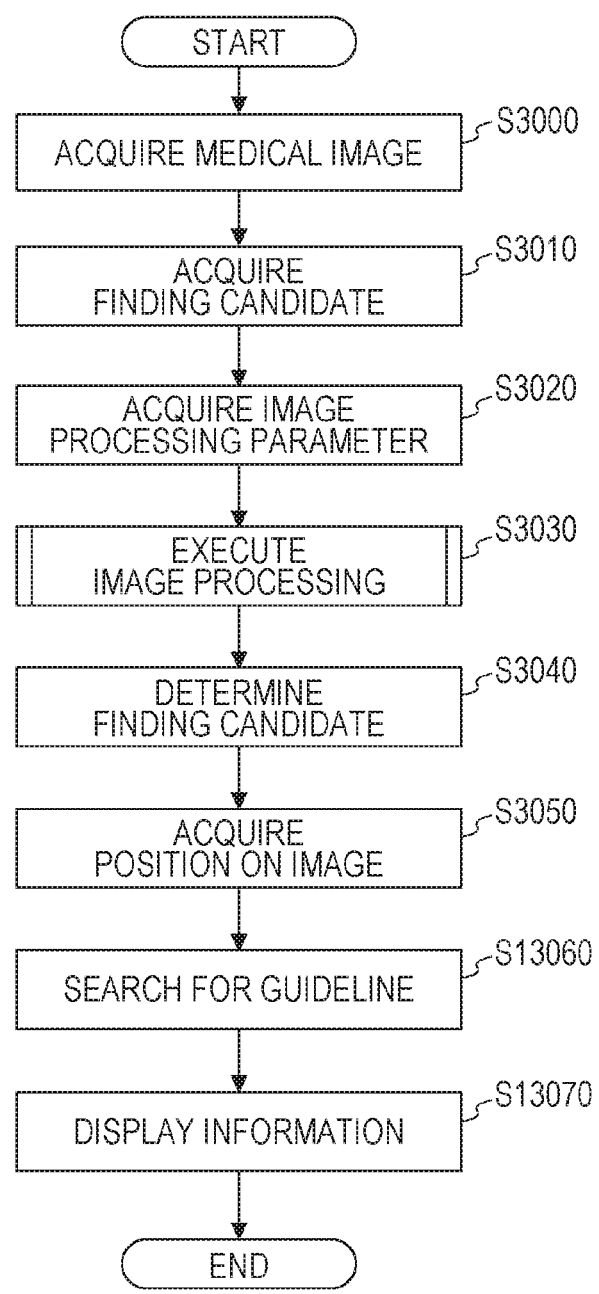
FIG. 13 is a flowchart showing an example of processing of a medical diagnosis support apparatus.

The diagnosis support apparatus 900 has a similar hardware configuration to that in FIGS. 2A and 2B according to the first embodiment. That is, the CPU 1001 executes the programs stored in the main memory 1002 and the magnetic disk 1003, and hence realizes the functions (the software) of the diagnosis support apparatus 900 and processing in the flowchart according to this embodiment. FIG. 13 shows a flowchart for describing an example of processing executed by the diagnosis support apparatus 900. This flowchart is basically similar to the first embodiment; however, part of the processing differs from the first embodiment. To be specific, this flowchart differs from the flow in FIG. 3A for search of a guideline (S13060) and display of information (S13070). For an example of processing executed by the diagnosis support apparatus 900 according to this embodiment, only part different from the first and second embodiments is described below with reference to the flowchart in FIG. 13 and an example of a display content in FIG. 14.

In the flowchart in FIG. 13, processing from step S3000 to step S3050 is similar to the processing according to the first and second embodiments. Hence, the description is omitted.

In step S13060, the searching unit 914 acquires a guideline from the database 300 by using the finding candidate determined as the corresponding finding in step S3040 as a key. The search key is, for example, "posterior vitreous detachment" or "macular hole." The number of findings each serving as a search key may be plural or one. The finding stored in the database 300 is, for example, a finding previously specified by a doctor for a case. It is assumed that the database 300 also includes information relating to the position of the finding specified by the doctor. Instead of the information on the finding previously specified by the doctor, the information on the finding included in the database 300 may be document information such as a textbook, or may be information on a finding specified by the doctor for a case collected for the database.

A method of acquiring a guideline may be acquiring only a guideline with a completely matched search key, or acquiring a guideline with a partly matched search key. For example, if a plurality of findings serve as search keys, the searching unit 914 may acquire a guideline matched to only part of a plurality of findings. Alternatively, the similarity may be calculated by a certain method, and guidelines may be acquired by a predetermined number in the descending order of similarity. For the method using the similarity, calculation can be made by using the degree of matching between the feature vectors like the method described in the modification of the second embodiment. In this embodiment, the similarity is described as the association degree.

In step S13070, the display control unit 116 controls the content to be displayed on the displaying unit 118. Then, the displaying unit 118 displays the display content controlled by the display control unit 116. This is described with reference to FIG. 14.

Figure 14:
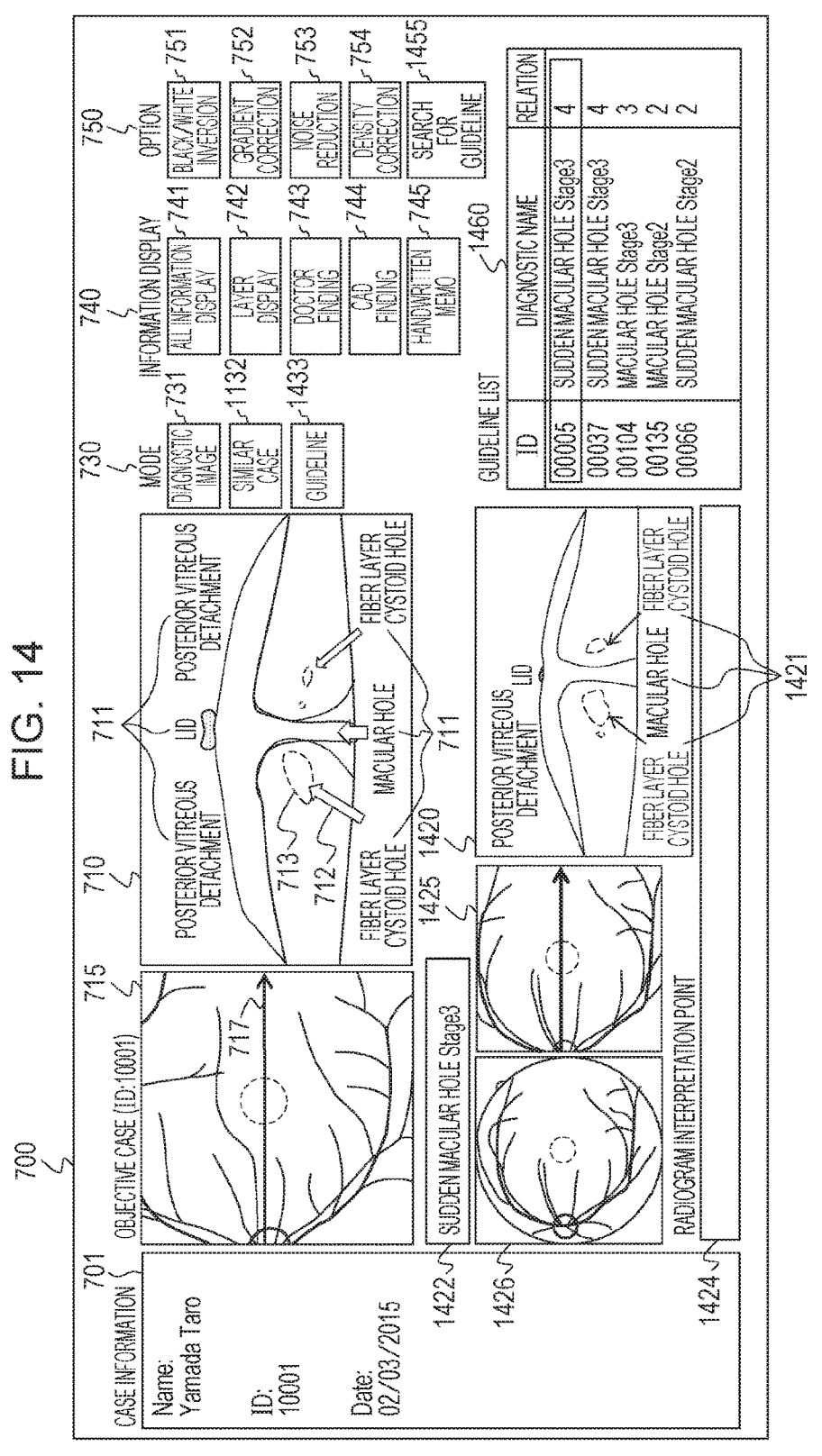

FIG. 14 illustrates an example of a display content displayed by the displaying unit 118. The display content 700 displayed by the displaying unit 118 is based on the illustration described with reference to FIG. 7 in the first embodiment. The third embodiment differs from the first embodiment in that a guideline mode 1433 is displayed as a user interface for selecting a guideline mode. When an operator selects the guideline mode by tapping or clicking the guideline mode 1433, the display control unit 116 causes a guideline list 1460 (that is, a list of cases in the descending order of the association degree of the guideline). Further, the display control unit 116 causes the displaying unit 118 to display a tomographic image 1420 of one of the cases in the guideline list, findings 1421, a diagnostic name 1422 of the case, a radiogram inspection point 1424, and a fundus image 1425 and a fundus picture 1426 corresponding to the tomographic image. The radiogram inspection point 1424 includes, for example, information on a desirable procedure of a radiogram inspection. The guideline list 1460 includes the IDs, diagnostic names, and association degrees of the cases. The association degree is equivalent to the similarity. In this embodiment, the association degree (the similarity) is indicated by five-level evaluation. For example, since the similarity is normalized by 1, a case with a similarity of 0.9 or higher is evaluated as 5, a case with a similarity from 0.8 to 0.9 is evaluated as 4, a case with a similarity from 0.6 to 0.8 is evaluated as 3, a case with a similarity from 0.4 to 0.6 is evaluated as 2, and a case with a similarity of 0.4 or lower is evaluated as 1. These numerical values are merely examples. The similarity may be directly displayed, or the evaluation may be made in ten levels instead of five levels. Also, if display is provided by using the similarity, cases with similarities of a certain value or higher may be displayed in the list and cases with low correlation may not be displayed in the list.

If the guideline mode 1433 is selected, a guideline search 1455 being an interface for executing guideline search is added to the option 750. By tapping or clicking the guideline search 1455, the guideline search relating to the objective tomographic image 710 is executed. In this embodiment, the example is described in which the user interface for executing the guideline search is different from the guideline mode 1433; however, the guideline search may be executed simultaneously when the guideline mode 1433 is selected.

In the tomographic image 710 with the findings superimposed, the information on the findings 711, which are determined as the corresponding findings on the basis of the information indicative of the positions of the findings, is superimposed under the above-described display rules. As described above, if another case in the guideline list is selected as the result of selection by a user input, the display control unit 116 controls the display content of the displaying unit 118. To be specific, the display control unit 116 causes the displaying unit 118 to display the tomographic image 1420 with the findings superimposed, the diagnostic name 1422, the radiogram inspection point 1424, and the fundus image 1425 and the fundus picture 1426 corresponding to the tomographic image, which correspond to the case selected in the guideline list 1160.

With this embodiment, the diagnosis support apparatus 900 acquires a corresponding finding candidate and an image processing parameter relating to derivation of the finding candidate on the basis of information on a portion of a medical image. Then, the diagnosis support apparatus 900 executes image processing in accordance with the acquired image processing parameter, determines the corresponding finding and specifies the position, searches for a guideline on the basis of the finding determined as the corresponding finding, and provides these results. Accordingly, the doctor can recognize the findings determined as the corresponding findings and their positions, the diagnostic name associated with the guideline, the image captured by another modality, and the radiogram inspection point on the medical image. Accordingly, since the doctor can view the state of the medical image being a current object and the diagnostic name of the similar case, the burden on diagnosis can be decreased.

The position of the finding may be used for search of a similar image as described in the second embodiment.

First Modification

In the third embodiment, a guideline with a matched finding is searched by using a finding as a search key. However, the method of guideline search is not limited thereto. For example, guideline search can be executed by selecting only a certain finding from a plurality of findings. When the guideline search is executed, if the guideline search is executed while the doctor finding display 743 is turned ON and the CAD finding display 744 is turned OFF, the guideline may be searched by using only a finding confirmed by the doctor. Also, if the guideline search is executed while the doctor finding display 743 is turned OFF and the CAD finding display 744 is turned ON, the guideline may be searched by using only a CAD finding. Further, if the guideline search is executed by selecting only a certain finding from the findings 711 displayed in the tomographic image, the guideline search can be executed by using only the selected certain finding. This modification may be applied to any other embodiment without limiting to the third embodiment.

Fourth Embodiment

Figure 15A:
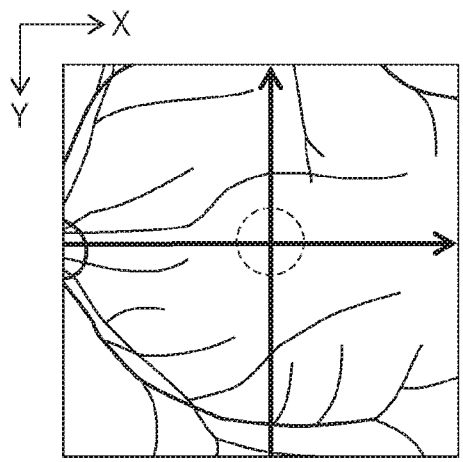
FIGS. 15A and 15B provide illustrations showing examples of imaging methods of an optical coherence tomography.
Figure 15B:
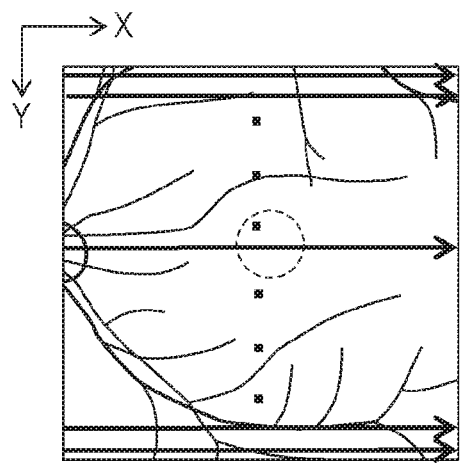

In the first to third embodiments, the support information such as the CAD finding is provided by using a single captured tomographic image. In an inspection using an optical coherence tomography, tomographic images may be captured and obtained in a plurality of directions in a single inspection. For example, as shown in FIG. 15A, two tomographic images may be occasionally acquired, one being a tomographic image passing through the optic disk and the fovea, the other one being a tomographic image passing through the fovea and being orthogonal to the tomographic image passing through the optic disk and the fovea. Also, as shown in FIG. 15B, three-dimensional imaging may be executed by executing raster scan (3D scan) on the fundus.

A diagnosis support apparatus according to this embodiment acquires a plurality of medical images captured in a plurality of directions or at a plurality of positions, provides support information on the medical images by using the image processing results of the acquired medical images, and hence supports a diagnosis relating to the medical images.

A functional configuration of a diagnosis support apparatus 900 according to this embodiment is similar to that in FIG. 9 according to the second embodiment. The diagnosis support apparatus 900 has a similar hardware configuration to that in FIGS. 2A and 2B according to the first embodiment. That is, the CPU 1001 executes the programs stored in the main memory 1002 and the magnetic disk 1003, and hence realizes the functions (the software) of the diagnosis support apparatus 900 and processing in the flowchart according to this embodiment. Also, a flowchart for describing an example of processing executed by the diagnosis support apparatus 900 is similar to any one of FIGS. 3A, 3B, 10, and 13. In this embodiment, search for a similar case in FIG. 10 is described. For processing executed by the diagnosis support apparatus 900 according to this embodiment, only part different from the first to third embodiments is described below with reference to the flowchart in FIG. 10. In this embodiment, an example of acquiring two tomographic images as shown in FIG. 15A and an example of acquiring a three-dimensional tomographic image as shown in FIG. 15B are described. That is, described here is an example in which the medical image acquiring unit 102 acquires a plurality of tomographic images at different positions of an eye to be inspected.

Cross scan in FIG. 15A is described first. In the following description, a tomographic image passing through the optic disk and the fovea is referred to as H-scan image, and a tomographic image passing through the fovea and orthogonal to the H-scan image is referred to as V-scan image.

In step S3000, the medical image acquiring unit 102 acquires a plurality of medical images captured by perform scanning with light in a plurality of directions transmitted from the optical coherence tomography apparatus 200, information relating to the type of the captured medical images, and information relating to the portions of the medical images. That is, the medical image acquiring unit 102 acquires the plurality of tomographic images obtained by performing scanning with measurement light in a different direction on an eye to be inspected. In this embodiment, the different direction is an orthogonal direction.

Information relating to the type of captured medical images and information relating to the portions of the medical images may be acquired by a single piece of information each for the plurality of medical images, or may be acquired by a number of pieces of information corresponding to the respective medical images. In the following description, a single piece of information relating to the type of medical images, and a single piece of information relating to the portion of the medical images, are obtained for the plurality of medical images.

Processing in step S3010 is similar to the processing in the first embodiment, and hence the description is omitted.

The processing from step S3020 to step S3050 are similar to those of the first embodiment except that processing is executed on each of the plurality of medical images, and hence the description is omitted.

In step S10060, the searching unit 914 acquires a similar image from the database 300 by using the finding candidate determined as the corresponding finding in step S3040 as a search key. In this embodiment, a similar image is acquired from the database 300 by using the finding candidate determined as the corresponding finding in a medical image among a plurality of medical images (that is, a medical image captured in a certain direction). In this embodiment, the similar image is acquired by using a finding obtained from the H-scan image. In this embodiment, it is noted that an image to be searched is only a medical image captured in the same direction as the direction in which the medical image being a search source is captured. That is, the searching unit 914 corresponding to an example of a similar image acquiring unit acquires a tomographic image obtained by performing scanning with measurement light in the same direction as the scanning direction of the measurement light when a tomographic image having an abnormal portion detected by the detecting unit is obtained, from the storage unit.

Also, similarly to the second embodiment, only an image with a completely matched search key is acquired as a similar image. If there are medical images corresponding to the similar image and captured in a direction different from the similar image, these medical images are acquired collectively as a single similar image.

In step S10070, the display control unit 116 controls the content to be displayed on the displaying unit 118. Then, the displaying unit 118 displays the display content controlled by the display control unit 116. To be specific, at least one of the plurality of medical images is displayed under control similar to the second embodiment. Also, similarly to the second embodiment, the display control unit 116 causes a similar image and information on a diagnostic name associated therewith to be displayed in the descending order of similarity.

Also, in this embodiment, similarly to the second embodiment, the similar image and the information on the diagnostic name associated therewith are managed in a list, information on the list is displayed, and one of cases in the list is displayed in a manner comparable with the plurality of medical images acquired in step S3000. That is, if there are a plurality of medical images captured in the different direction, at least one of the medical images is displayed in a comparable manner. The image to be displayed at this time is an image captured in the same direction as the plurality of medical images acquired in step S3000. Alternatively, an image captured in a different direction may be displayed.

In this embodiment, one of the plurality of medical images acquired in step S3000, and one of the plurality of medical images being the similar images determined as a case and displayed in a comparable manner are displayed. The image to be displayed is determined by the diagnosis support apparatus 900 or selection by a user input. The selection by a user input may be realized by using a user interface such as a button.

Figure 16:
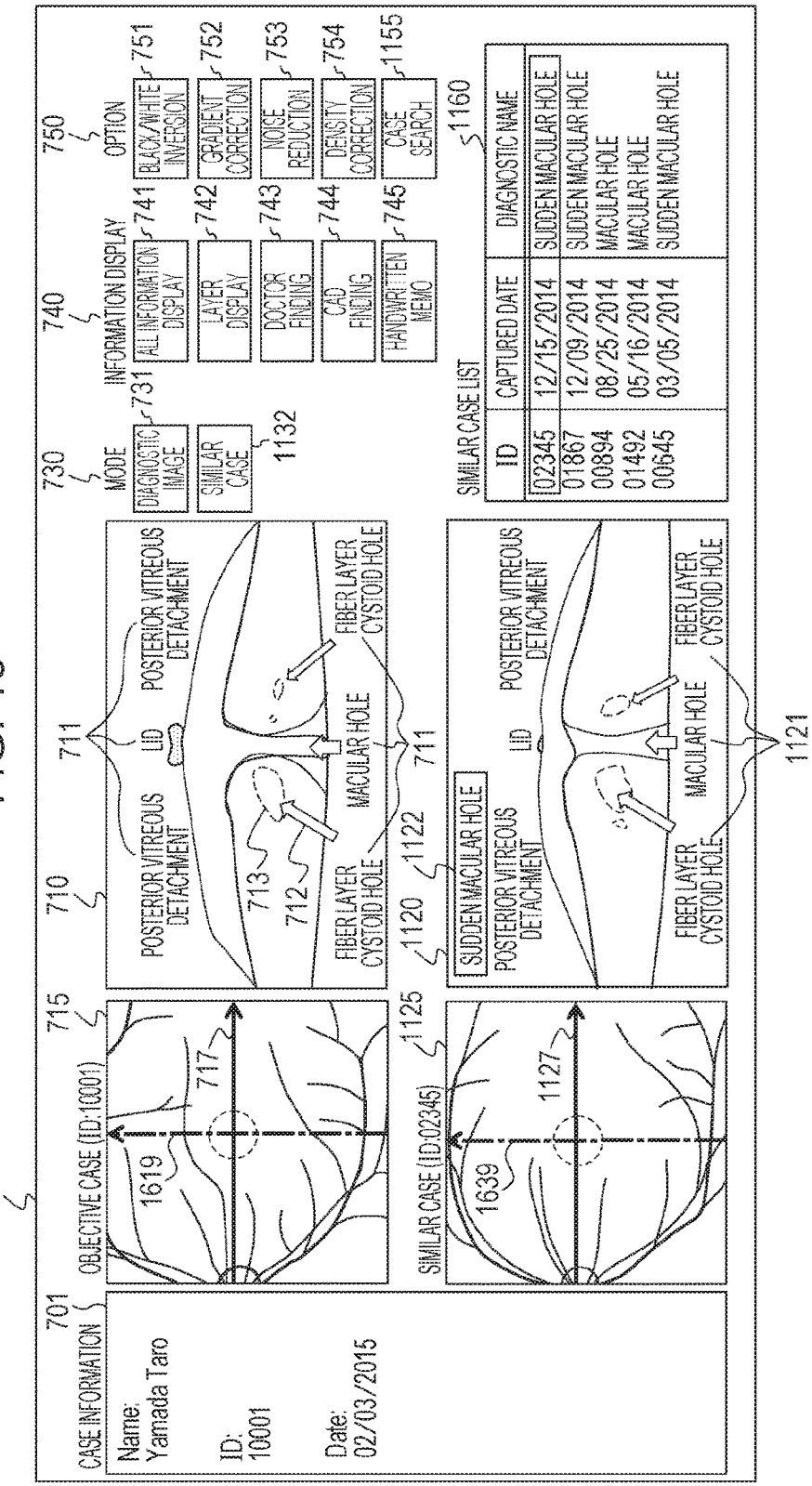
FIG. 16 is an illustration showing an example display of a displaying unit according to a fourth embodiment.

FIG. 16 illustrates an example of a display content displayed by the displaying unit 118. The display content 700 displayed by the displaying unit 118 includes a tomographic image 710 of an objective case, and a fundus image 715 corresponding to the tomographic image of the objective case.

An arrow 717 indicative of the captured direction of the tomographic image is superimposed on the fundus image 715. The horizontal arrow 717 corresponds to the H-scan image, and a vertical arrow 1619 corresponds to a V-scan image. Also, the display content 700 includes a similar case list 1160. Further, similarly to the objective case, the display content 700 includes a tomographic image 1120 and its diagnostic name 1122 of a single case determined among the similar case list, and a fundus image 1125, a horizontal arrow 1127, and a vertical arrow 1639 corresponding to the tomographic image. Superimposition of findings on the tomographic images 710 and 1120, and selection by the user from the similar case list are similar to the second embodiment, and hence the description is omitted.

In an initial state (that is, a state before selection is made by a user input) of the tomographic image 1120, the display control unit 116 causes the displaying unit 118 to display the tomographic image in a direction in which the tomographic image 710 including the finding used for the search in step S10060 is captured. That is, if the tomographic image 710 is an H-scan image, the tomographic image 1120 is also an H-scan image. In this embodiment, as described above, a single medical image of a plurality of medical images can be displayed by selection by a user input. To be specific, the horizontal arrows 717 and 1127 and the vertical arrows 1619 and 1639 superimposed on the fundus images 715 and 1125 are selected, for example, by clicking on the mouse or tapping. If the vertical arrows 1619 and 1639 are selected, the display control unit 116 causes the displaying unit 118 to display medical images (V-scan images) captured in the direction corresponding to the clicked arrow as the tomographic images 710 and 1120. In this case, it is desirable to display the currently selected arrows in a manner distinguishable from the other arrows. In the example in FIG. 16, arrows indicated by solid lines are selected arrows, and arrows indicated by dotted-chain lines are not selected arrows. Alternatively, by selecting one of the vertical arrows 1619 and 1639, both tomographic images 710 and 1120 may be changed to V-scan images in an associated manner.

Only a common finding among the findings of the V-scan images and the findings of the H-scan images may be displayed on each tomographic image. That is, on the basis of a plurality of abnormal portions obtained from a plurality of tomographic images, the display control unit 116 may cause the displaying unit to display a finding of an abnormal portion common to the plurality of tomographic images.

The case of three-dimensional scan shown in FIG. 15B is described next. For processing executed by the diagnosis support apparatus 900 according to this embodiment, only part different from the second embodiment is described below with reference to the flowchart in FIG. 10. In the three-dimensional scan, the following processing is described while it is assumed that positioning processing has been executed among a plurality of tomographic images by the image processing unit 108 or a positioning unit (not shown).

Processing in step S3010 is similar to the processing in the first embodiment, and hence the description is omitted.

In step S3020, processing similar to the other embodiments is executed on each of a plurality of medical images. However, the image processing parameter stored in the second table information may include a parameter in the Y-direction as a spatial parameter. For example, if image capturing is executed at the center of the macula because a macular hole is generated at the macula portion, a macula is present around the center of both the X- and Y-axes. Accordingly, the region can be limited to the imaging range of X: 40% to 60% and Y: 40% to 60%. The image processing parameter is applied to only the tomographic image included in the range.

In step S3030, structural analysis is executed on the plurality of tomographic images acquired by raster scan, and hence an abnormal portion of the eye to be inspected is detected. That is, the image processing described in the other embodiments is applied to each of the plurality of tomographic images.

In step S3030, three-dimensional image processing may be executed. The luminance is not normalized for each of the plurality of tomographic images. The histogram is adjusted entirely for the plurality of tomographic images. Also, respective filters used for image processing may be three-dimensionally defined.

In step S3040, a finding is also three-dimensionally determined. For example, determination itself may be made for each of the plurality of tomographic images, and determination may be made again for regions of adjacent finding candidates in adjacent tomographic images. Alternatively, a finding candidate may be determined by using a size ratio or the like of a three-dimensionally connected region, for a disease candidate detected in step S3030.

In step S3050, the position acquiring unit 112 acquires information indicative of the position of a finding in a medical image on the basis of the result of the image processing executed in step S3030 and the finding candidate determined as the corresponding finding in step S3040. The information indicative of the position may be any type of information as long as the position can be specified. In this embodiment, the information indicative of the position is acquired as information indicative of a position of a rectangular parallelepiped or a cube adjacent to the image processing region determined as corresponding to the finding.

In step S10060, the searching unit 914 acquires a similar image from the database 300 by using the finding candidate determined as the corresponding finding in step S3040 as a search key. In this embodiment, the searching unit 914 acquires a similar image from the database 300 by using the finding candidate determined as the corresponding finding from a plurality of medical images. Also, similarly to the second embodiment, only an image with a completely matched search key or an image with a high similarity is acquired as a similar image. In a similar image having a similar finding feature or a similar image feature, if there are a plurality of images captured in a different direction or a plurality of images captured in the same direction, the searching unit 914 collectively acquires the images as a single similar image.

In step S10070, the display control unit 116 controls the content to be displayed on the displaying unit 118. Then, the displaying unit 118 displays the display content controlled by the display control unit 116. To be specific, at least one of the plurality of medical images is displayed under control similar to the second embodiment. Also, similarly to the second embodiment, the display control unit 116 causes a similar image and information on a diagnostic name associated therewith to be displayed in the descending order of similarity.

Also, in this embodiment, similarly to the second embodiment, the similar image and the information on the diagnostic name associated therewith are managed in a list, information on the list is displayed, and one of cases in the list is displayed in a manner comparable with the plurality of medical images acquired in step S3000. In this embodiment, one of the plurality of medical images acquired in step S3000, and one of the plurality of medical images being the similar images determined as the one case to be displayed in a comparable manner are displayed. The image to be displayed is determined by the diagnosis support apparatus 900 or selection of a user input. The selection by a user input may be realized by using a user interface such as a button.

Figure 17:
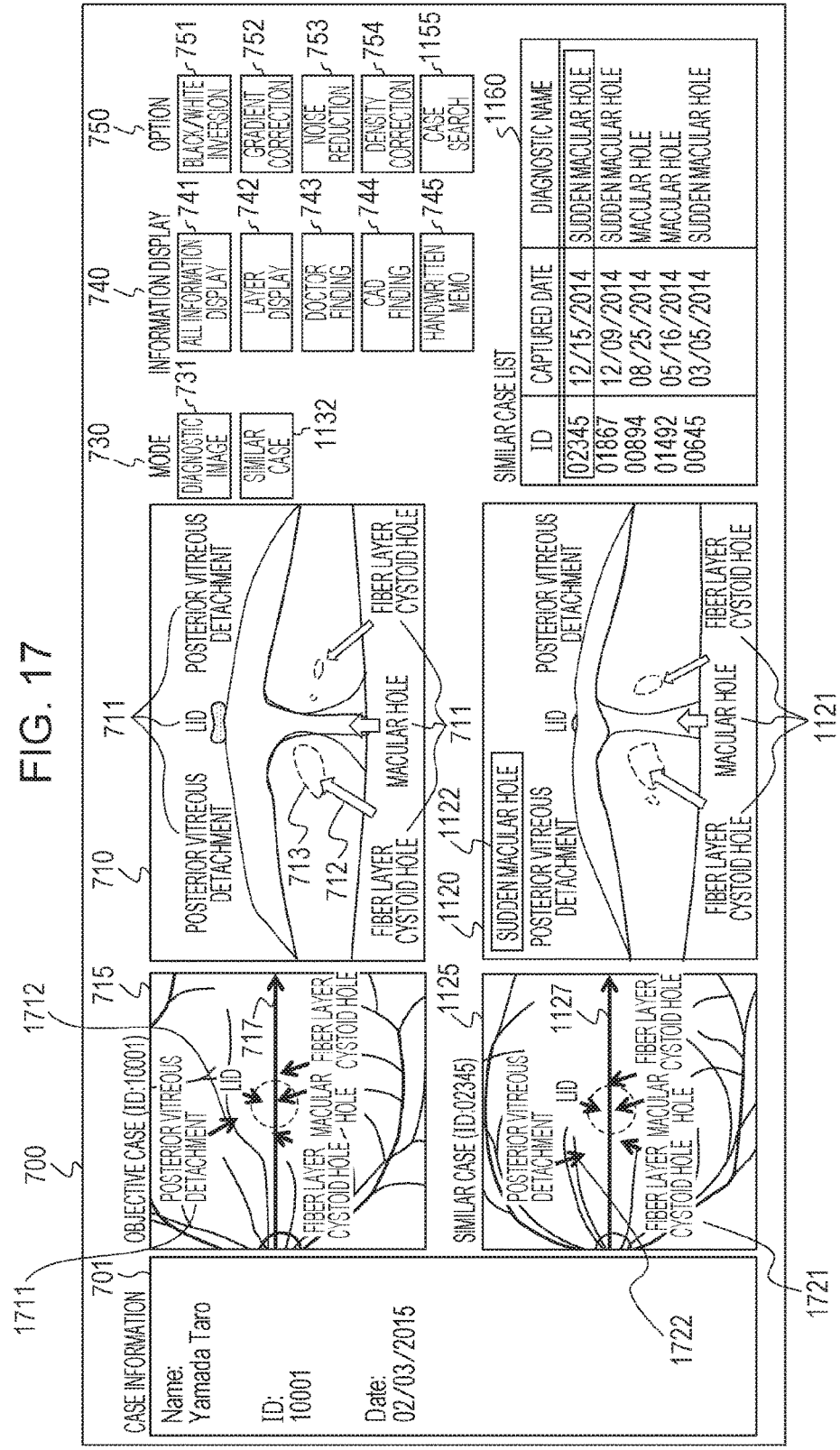
FIG. 17 is an illustration showing an example display of the displaying unit according to the fourth embodiment.

FIG. 17 illustrates an example of a display content displayed by the displaying unit 118. The display content 700 displayed by the displaying unit 118 includes a tomographic image 710 of an objective case, and a fundus image 715 corresponding to the tomographic image of the objective case. The fundus image 715 is an integrated image generated by integrating a plurality of tomographic images acquired by the medical image acquiring unit 102 in the depth direction. The medical image acquiring unit 102 may generate an integral image. Since the fundus image 715 is an image generated on the basis of the tomographic image, the position of the finding on the tomographic image can be associated with the position on the fundus image 715. Also, the fundus image 715 may be an image captured by SLO or a fundus camera. In this case, the medical image acquiring unit 102 acquires a fundus image from the SLO or the fundus camera (not shown). That is, the medical image acquiring unit 102 acquires a fundus image of an eye to be inspected. By positioning the fundus image obtained by the SLO or the fundus camera and the integral image generated on the basis of the tomographic image, the finding on the tomographic image can be associated with the fundus image 715 obtained by the SLO or the fundus camera. As described above, since the finding on the tomographic image can be associated with the fundus image 715, the display control unit 116 can cause the finding to be displayed on the fundus image 715. That is, the display control unit can cause the displaying unit to further display a fundus image, and also display a finding on the fundus image.

An arrow 717 indicative of the position of the tomographic image 710 at the fundus, a finding 1711, and a marker 1712 are superimposed on the fundus image 715, The marker 1712 is displayed to indicate the position of the center of gravity of the rectangular parallelepiped or the cube indicative of the region of the position of the finding acquired in step S3050.

In this embodiment, the position at which the corresponding finding is superimposed on the fundus image 715 is determined for the corresponding finding under display rules as follows. Of course, the display rules are not limited to the example described below. (1) Superimposition is not provided on character information of another finding determined as the corresponding finding. (2) For information indicative of the position of a finding determined as the corresponding finding, a marker (for example, an arrow) is added to a position near the information indicative of the position of the finding. (3) If a plurality of the same findings are present, a funding at a representative position in a spatially close region is displayed. (4) If there are present the same findings by a number larger than N, the number of findings to be displayed is N or smaller.

For the rule (3), for example, a plurality of hard exudates may be present in a close region. In this case, the spatially close hard exudates are collectively displayed. To be specific, if five hard exudates are present in a circle with a diameter of 1 mm in an XY plane, only one finding is displayed on a fundus image instead of five findings. That is, if findings corresponding to abnormal portions detected by the detecting unit from different tomographic images are the same findings, and the distance between the abnormal portions detected from the different tomographic images is smaller than a threshold, the display control unit 116 causes the same findings to be displayed as one finding on the fundus image. The findings may be grouped if the distance between the hard exudates is equal to or smaller than a threshold, or the findings may be grouped if the distance between the plurality of tomographic images with the hard exudates detected is equal to or smaller than a threshold.

Regarding the above-described rule (4), even if findings appear in a wide range although the spatially close findings are grouped under the above-described rule (3), findings are displayed by a number larger than the number N. In this case, the number of the same findings to be displayed is adjusted to be the number N or smaller. For example, N is three. If the number of findings to be displayed is larger than three, the findings spatially close to the macula fovea may be left, or one finding close to the macula fovea may be selected and the other two findings being spatially separated may be left. For example, one finding at the center is selected, and two residual findings are selected from upper and lower sides by one each. The finding close to the fovea has larger influence on the viewing function than the other findings, and hence the finding is information required for the doctor or the like.

The finding 1711 and the marker 1712 superimposed on the fundus image can be turned ON/OFF by the user interface of the information display 740 as described above in the first embodiment. Also, display of the finding by the doctor and the finding by the CAD can be also turned ON/OFF. Display of these findings may be turned ON/OFF in accordance with the number of times of clicking. For example, as the number of times of clicking increases, the display may be changed from "both are ON," to "finding on tomographic image is ON and finding on fundus image is OFF," "finding on tomographic image is OFF and finding on fundus image is ON," and then "both are OFF." Alternatively, the type of finding to be turned ON/OFF may be designated by a user interface (not shown). The CAD finding output from the computer can be confirmed (approved) or the CAD finding can be corrected. The processing can be executed by using any of the finding 711 superimposed on the tomographic image 710 and the finding 1711 superimposed on the fundus image 715. If the confirmation (or correction) is made with any of the findings 711 and 1711, the corresponding finding is also confirmed (corrected). That is, when the color of characters of the finding is changed between the CAD finding and the doctor finding, it is considered that, if "lid" of the finding 1711 is confirmed, "lid" of the finding 711 is also confirmed. The display control unit 116 changes the characters of both the findings. In the case of the three-dimensionally captured data, since a lesion three-dimensionally extends, the same finding is displayed in a plurality of tomographic images. For example, "lid" is displayed in adjacent five tomographic images. In this case, if confirmation is made with the fundus image or confirmation is made with any one of the tomographic images, the display control unit 116 similarly causes the displaying unit 118 to display the finding with the color indicative of the confirmed finding in the other tomographic images.

The slice position of the plurality of tomographic images can be changed by operating a slider bar (not shown) or the arrow 717. Alternatively, the position of the tomographic image may be changed by selecting the finding 1711. That is, by tapping or clicking the finding 1711 on the fundus image, the tomographic image including the finding 1711 is displayed. In this case, the display control unit 116 causes the displaying unit 118 to display the tomographic image corresponding to the position of the center of gravity of a rectangular parallelepiped or a cube adjacent to an image processing region determined as corresponding to the selected finding 1711. Accordingly, the tomographic image to be focused can be quickly displayed on the basis of the fundus image and the finding.

Also, the display content 700 includes a similar case list 1160. Further, similarly to the objective case, the display content 700 includes a tomographic image 1120 and its diagnostic name 1122 of a single case determined among the similar case list, and a fundus image 1125 corresponding to the tomographic image, an arrow 1127 indicative of the position of the tomographic image 1120, and a finding 1721. The superimposition of the findings on the tomographic images 710 and 1120, and the selection by the user on the similar case list are similar to the second embodiment, and hence the description is omitted.

In this embodiment, as described above, a single medical image of a plurality of medical images can be displayed by selection by a user input.

With this embodiment, if a medical image includes a plurality of images, not only an image captured in the direction as the search object, but also an image captured in another direction can be recognized by a simple operation. That is, the findings spread in a wide range can be recognized, and hence the burden on diagnosis can be decreased.

First Modification

In step S10060 according to the fourth embodiment, the searching unit 914 acquires the similar image from only the medical images captured in the same direction in the database 300 by using the finding candidate determined as the corresponding finding in one of the plurality of medical images as the search key. However, the finding to be used may not be only the finding determined as the corresponding finding in the single medical image. For example, a search key may be created in each of at least two images among a plurality of medical images or in each of all medical images, and a similar image may be acquired in all directions. For example, a case is considered in which a plurality of medical images being search sources include an H-scan image and a V-scan image. In this case, the searching unit 914 acquires a medical image having an H-scan image similar to the H-scan image being the search source and a V-scan image similar to the V-scan image being the search source, as a similar image from among images present in the database 300.

Also, in the fourth embodiment, only medical images captured in the same direction as the direction in which the medical images being the search sources are captured, from the database 300. However, a medical image captured in another direction may be an object to be acquired from the database 300. For example, if an image being a search source is an H-scan image, a V-scan image present in the database 300 may be acquired as a similar image. Further, the searching unit 914 may not use only the finding determined as the corresponding finding in the single medical image. Findings determined as corresponding findings in two or more images of a plurality of medical images or in all medical images may serve as search keys after removal of AND and OR.

Fifth Embodiment

Figure 18:
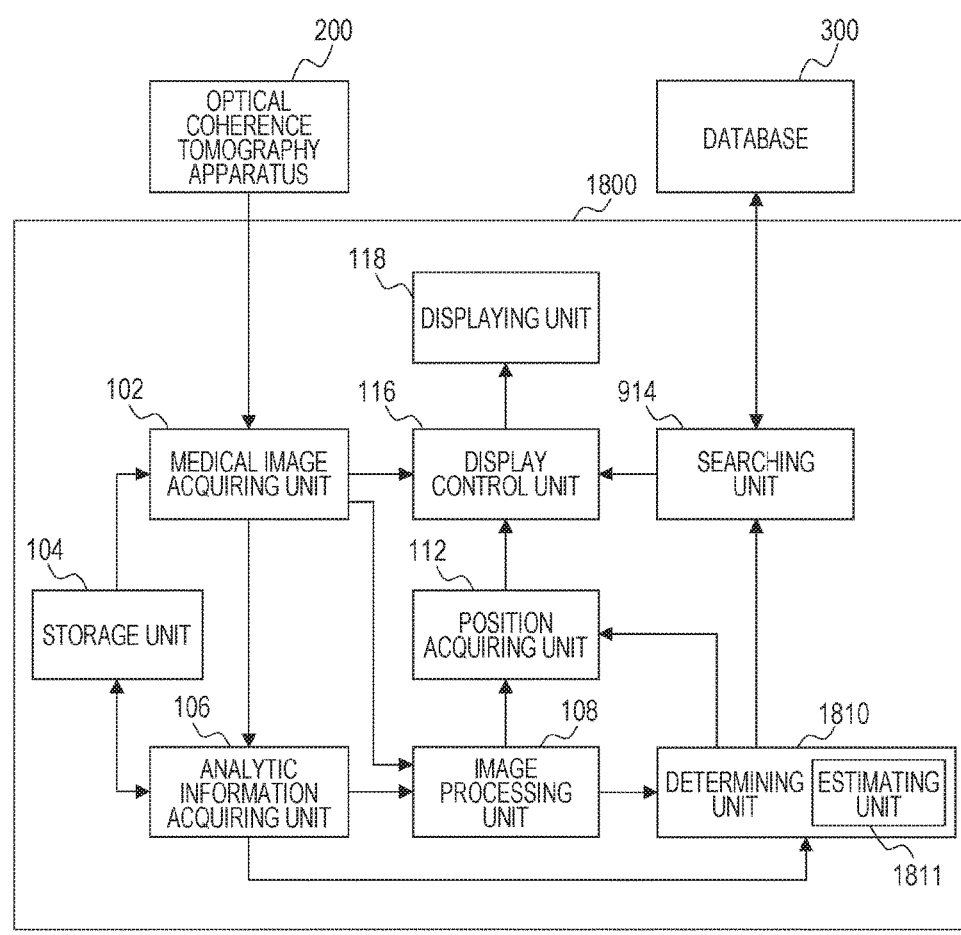
FIG. 18 is an illustration showing an example of a functional configuration of a medical diagnosis support apparatus.

In the fourth embodiment, the plurality of medical images captured in the plurality of directions are acquired, and the support information such as the CAD finding is provided on the medical image by using the image processing results of the acquired medical images. In this embodiment, with use of an image processing result of an acquired medical image, by providing support information on the medical image and estimating and providing a disease name (a diagnostic name), diagnosis support relating to the medical image is executed. An example of a functional configuration of a diagnosis support apparatus 1800 according to a fifth embodiment is described with reference to FIG. 18. The diagnosis support apparatus 1800 includes an estimating unit 1811 in addition to the functional configuration shown in FIG. 9. The estimating unit 1811 realized by the CPU 1001 executing a program estimates a disease name by using an abnormal portion detected from a tomographic image. FIG. 19 shows a flowchart for describing an example of processing executed by the diagnosis support apparatus 1800. This flowchart is basically similar to the first embodiment; however, part of the processing differs from the first embodiment. To be specific, step S19060 of estimating a disease name candidate and a step S19070 of displaying information differ from the first embodiment. For an example of entire processing executed by the diagnosis support apparatus 1800 according to this embodiment, only part different from the first to fourth embodiments is described below with reference to the flowchart in FIG. 19 and an example of a display content in FIGS. 20A to 20D, and 21. In this embodiment, cross scan as shown in FIG. 15A is described. This embodiment can be applied to any of other scan patterns.

The processing from step S3000 to S3050 is similar to the fourth embodiment, and hence the description is omitted.

Figure 20A:
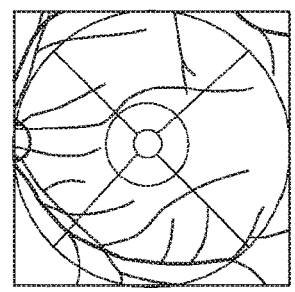
FIGS. 20A to 20D are illustrations for describing estimation processing according to a fifth embodiment.
Figure 20B:
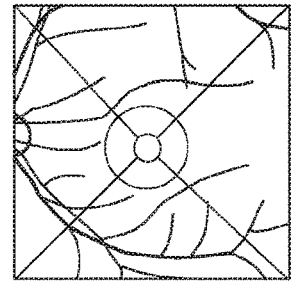

In step S19060, the estimating unit 1811 estimates a disease name candidate on the basis of an obtained finding. That is, the estimating unit 1811 corresponds to an example of an estimating unit configured to estimate a disease name on the basis of a finding. The estimating unit 1811 estimates a disease name candidate for an H-scan image and a V-scan image acquired in step S3050 by using the positions of finding candidates of the images. That is, the estimating unit 1811 estimates a disease name candidate on the basis of the position and the finding on a fundus image. Specification of the position of the finding on the fundus image is described with reference to FIGS. 20A to 20D. FIGS. 20A to 20D show a plurality of examples each dividing the region of a fundus image. FIGS. 20A and 20B each are an example, in which the region of the fundus image is divided toward the ear side, upper side, nose side, and lower side with respect to the macula fovea, into sectors depending on the distance from the macula fovea. For example, a sector has a diameter of 1 mm, 3 mm, or 10 mm. The numerical value is not limited to the above-described values. FIG. 20A is an example of dividing a circular region with reference to the macula fovea. FIG. 20B is an example of dividing the entire region outside a region with a diameter of 3 mm from the fovea.

Figure 20C:
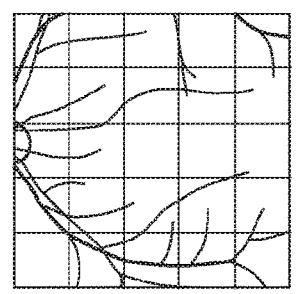
Figure 20D:
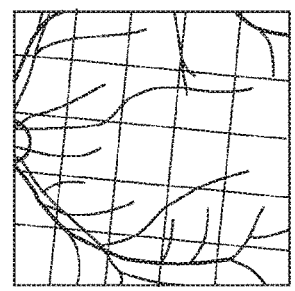

Also, FIGS. 20C and 20D each are an example, in which the entire fundus image is divided into a grid. FIG. 20C is an example of dividing the region of the fundus image by horizontal and vertical lines in the imaging range of the fundus image. FIG. 20D is an example of dividing the region of the fundus image by horizontal and vertical lines with respect to the line connecting the optic disk portion and the macula fovea. As described here, the fundus image is divided into desirable regions with respect to at least one of the macula portion and the optic disk portion.

A case is described in which the region of the fundus image is divided as shown in FIG. 20A. For example, if a retinal hyperplasia part is detected at the upper side or lower side and a foveal cystoid hole is detected at the center of a V-scan image, and if a foveal cystoid hole is detected in an H-scan image, the estimating unit 1811 estimates (detects) a disease name candidate as branch retinal vein occlusion. In this way, the estimating unit 1811 estimates the disease name on the basis of the finding in the V-scan image and the finding in the H-scan image. That is, the estimating unit 1811 estimates a disease name on the basis of a finding of an abnormal portion obtained from each of a plurality of tomographic images.

The estimating unit 1811 may use a decision tree method such as Random forests, or an identifier such as a support vector machine (SVM) to estimate a disease name candidate. Alternatively, the estimating unit 1811 may execute similar case search by using a finding or an image feature, execute search with regard to a spatial feature at which a finding appears in a fundus image, and provide a disease name associated with the search result. In a case of cross scan, the spatial feature represents similarities calculated for a feature vector in a center, upper side, and lower side region and a feature vector in a center, nose side, and ear side region.

In step S19070, the display control unit 116 controls the content to be displayed on the displaying unit 118. Then, the displaying unit 118 displays the display content controlled by the display control unit 116. To be specific, at least one of the plurality of medical images is displayed under control similar to the second embodiment. FIG. 21 illustrates an example of a display content displayed by the displaying unit 118. The display content 700 displayed by the displaying unit 118 includes a tomographic image 2110 of an objective case, a finding 2111, a marker 2112, and a fundus image 2115 corresponding to the tomographic image being the objective case. An arrow 2117 indicative of the position of the displayed tomographic image 2110 (H-scan image) is superimposed on the fundus image 2115. Similarly, for the V-scan image, the display content 700 includes a tomographic image 2120, a finding 2121, a marker 2122, and a fundus image 2115 corresponding to the tomographic image being the objective case. An arrow 2119 indicative of the position of the displayed tomographic image 2120 (V-scan image) is superimposed on the fundus image 2115. As shown in FIG. 21, a hemorrhage region 2116 is found in a wide range of a bottom portion of the fundus image 2115. Also, the display content 700 includes a diagnostic name candidate mode 2134 and a diagnostic name candidate list 2160. A diagnostic name candidate mode is selected by tapping or clicking the diagnostic name candidate mode 2134. Accordingly, the above-described processing of displaying diagnostic name candidates is executed.

In this embodiment, the H-scan image and the V-scan image are displayed. However, it is not limited thereto. For example, a plurality of tomographic images may be displayed in an upper portion of the screen (for example, at the position of the tomographic image 2110), and the tomographic images may be switched and displayed by a user interface (not shown). That is, one of the H-scan image 2110 and the V-scan image 2120 may be displayed, and the images to be displayed may be switched by the user interface. Also, the guideline of the diagnosis corresponding to the diagnostic name candidate list may be displayed in a lower portion of the screen as described in the third embodiment. By switching the selection of the diagnostic name displayed in the diagnostic name candidate list, the guideline of the diagnosis is switched.

With this embodiment, the finding is displayed and the diagnostic name candidate is displayed. Further, the guideline of the relating diagnosis can be referenced. The burden on diagnosis of the doctor can be decreased. Also, with this embodiment, since the disease name is estimated on the basis of the two orthogonal tomographic images, the disease name can be further correctly estimated.

Other Embodiments

All the functions or part of the functions described above may be placed in a network. In this case, a server client configuration may be employed in which only the display function or part of the functions may be operated at the local side. Also, the above-described respective embodiments may be individual embodiments, or may be combined.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An image processing apparatus comprising:
   a first acquiring unit configured to acquire a tomographic image of an eye to be inspected;
   a detecting unit configured to execute structural analysis on the acquired tomographic image and detect an abnormal portion of the eye;
   a second acquiring unit configured to acquire a similar case image related to a similar case of the detected abnormal portion, using finding information about a finding of the detected abnormal portion and position information about a position of the detected abnormal portion; and
   a display control unit configured to cause a displaying unit to display the acquired tomographic image and the acquired similar case image,
   wherein the display control unit causes the displaying unit to display a fundus image corresponding to the acquired tomographic image and a fundus image corresponding to the acquired similar case image together with the acquired tomographic image and the acquired similar case image,
   wherein the display control unit causes the displaying unit to display first information on the fundus image corresponding to the acquired tomographic image,
   wherein the display control unit causes the displaying unit to display second information on the fundus image corresponding to the acquired similar case image, and
   wherein the first information is information about a scanning of measurement light when the acquired tomographic image is obtained, and the second information is information about a scanning of measurement light when the acquired similar case image is obtained.

2. The image processing apparatus according to claim 1, wherein the second acquiring unit searches for a similar case having a finding matched to the finding of the detected abnormal portion and a position similar to the position of the detected abnormal portion, and acquires the similar case image related to the similar case which has found through the search.

3. The image processing apparatus according to claim 1, wherein the second acquiring unit acquires the similar case image obtained by performing scanning with measurement light in a direction the same as a scanning direction of measurement light when the acquired tomographic image is obtained.

4. The image processing apparatus according to claim 1, wherein the display control unit further causes the displaying unit to display a diagnosis name of the similar case.

5. The image processing apparatus according to claim 1, wherein the display control unit causes the displaying unit to display the acquired tomographic image and the acquired similar case image arranged side by side in a comparable manner.

6. The image processing apparatus according to claim 1, wherein the display control unit causes the displaying unit to display the finding information at a position on the acquired tomographic image, where at least a part of the finding information does not overlap a region indicating the detected abnormal portion.

7. The image processing apparatus according to claim 1, wherein the first information is information about at least one of a scanning position and a scanning direction of measurement light when the tomographic image is obtained, and the second information is information about at least one of a scanning position and a scanning direction of measurement light when the acquired similar case image is obtained.

8. An image processing apparatus comprising:
a first acquiring unit configured to acquire a tomographic image of an eye to be inspected;
a detecting unit configured to execute structural analysis on the acquired tomographic image and detect an abnormal portion of the eye; and
a display control unit configured to cause a displaying unit to display the acquired tomographic image,
wherein the display control unit causes the displaying unit to display finding information about a finding of the detected abnormal portion in a region in the acquired tomographic image other than a region between one of an internal limiting membrane and a nerve fiber layer boundary and one of a retinal pigment epithelium boundary and a photoreceptor inner segment/outer segment boundary included in the tomographic image.

9. An image processing apparatus comprising:
a first acquiring unit configured to acquire a tomographic image of an eye to be inspected;
a detecting unit configured to execute structural analysis on the acquired tomographic image and detect an abnormal portion of the eye;
a display control unit configured to cause a displaying unit to display the acquired tomographic image
an extracting unit configured to extract a layer boundary from the acquired tomographic image,
wherein the detecting unit executes the structural analysis with different algorithms on a first region and a second region in the acquired tomographic image, and detects a first abnormal portion from the first region and a second abnormal portion different from the first abnormal portion from the second region, and
wherein the first region and the second region are defined by the extracted layer boundary.

10. An image processing method comprising:
acquiring a tomographic image of an eye to be inspected;
executing structural analysis on the acquired tomographic image and detecting an abnormal portion of the eye;
acquiring a similar case image related to a similar case of the detected abnormal portion, using finding information about a finding of the detected abnormal portion and position information about a position of the detected abnormal portion; and
causing a displaying unit to display the acquired tomographic image and the acquired similar case image,
wherein the causing includes causing the displaying unit to display a fundus image corresponding to the acquired tomographic image and a fundus image corresponding to the acquired similar case image together with the acquired tomographic image and the acquired similar case image,
wherein the causing includes causing the displaying unit to display first information on the fundus image corresponding to the acquired tomographic image,
wherein the causing includes causing the displaying unit to display second information on the fundus image corresponding to the acquired similar case image, and
wherein the first information is information about a scanning of measurement light when the acquired tomographic image is obtained, and the second information is information about a scanning of measurement light when the acquired similar case image is obtained.

11. A non-transitory storage medium non-temporarily storing a program for causing computer to execute the image processing method according to claim 9.

12. An image processing apparatus comprising:
an acquiring unit configured to acquire, by performing analysis on a tomographic image of an eye to be inspected, a similar case image related to a similar case of an abnormal portion of the eye; and
a display control unit configured to cause a displaying unit to display the tomographic image and the acquired similar case image,
wherein the display control unit causes the displaying unit to display a fundus image corresponding to the tomographic image and a fundus image corresponding to the acquired similar case image together with the tomographic image and the acquired similar case image,
wherein the display control unit causes the displaying unit to display first information on the fundus image corresponding to the tomographic image,
wherein the display control unit causes the displaying unit to display second information on the fundus image corresponding to the acquired similar case image, and
wherein the first information is information about a scanning of measurement light when the tomographic image is obtained, and the second information is information about a scanning of measurement light when the acquired similar case image is obtained.

13. The image processing apparatus according to claim 12, wherein the first information is information about at least one of a scanning position and a scanning direction of measurement light when the tomographic image is obtained, and the second information is information about at least one of a scanning position and a scanning direction of measurement light when the acquired similar case image is obtained.

14. The image processing apparatus according to claim 12, further comprising:
a detecting unit configured to detect the abnormal portion of the eye by the performing the analysis on the tomographic image;
wherein the acquiring unit acquires, by using the detected abnormal portion, the similar case image.

15. An image processing apparatus comprising:
an acquiring unit configured to acquire finding information about a finding of an abnormal portion of an eye to be inspected by performing analysis on a tomographic image of the eye; and
a display control unit configured to cause a displaying unit to display the tomographic image,
wherein the display control unit causes the displaying unit to display the finding information in a region in the tomographic image other than a region between one of an internal limiting membrane and a nerve fiber layer boundary and one of a retinal pigment epithelium boundary and a photoreceptor inner segment/outer segment boundary included in the tomographic image.

16. The image processing apparatus according to claim 15, further comprising:
a detecting unit configured to detect the abnormal portion of the eye by the performing the analysis on the tomographic image;
wherein the acquiring unit acquires, by using the detected abnormal portion, the finding information.

17. An image processing apparatus comprising:
a detecting unit configured to detect an abnormal portion of an object to be inspected by performing analysis on a tomographic image of the object;
a display control unit configured to cause a displaying unit to display the tomographic image,
wherein the detecting unit detects, by performing the analysis with different algorithms on a first region and a second region in the tomographic image, a first abnormal portion from the first region and a second abnormal portion different from the first abnormal portion from the second region.

18. The image processing apparatus according to claim 17,
wherein the first region and the second region are defined by a boundary in the tomographic image.

19. An image processing method comprising:
acquiring finding information about a finding of an abnormal portion of an eye to be inspected by performing analysis on a tomographic image of the eye; and
causing a displaying unit to display the tomographic image,
wherein the causing includes causing the displaying unit to display the finding information in a region in the tomographic image other than a region between one of an internal limiting membrane and a nerve fiber layer boundary and one of a retinal pigment epithelium boundary and a photoreceptor inner segment/outer segment boundary included in the tomographic image.

20. A non-transitory storage medium non-temporarily storing a program for causing a computer to execute the image processing method according to claim 19.

21. An image processing method comprising:
detecting an abnormal portion of an object to be inspected by performing analysis on a tomographic image of the object;
causing a displaying unit to display the tomographic image,
wherein the detecting includes detecting, by performing the analysis with different algorithms on a first region and a second region in the tomographic image, a first abnormal portion from the first region and a second abnormal portion different from the first abnormal portion from the second region.

22. A non-transitory storage medium non-temporarily storing a program for causing a computer to execute the image processing method according to claim 21.

* * * * *